United States Patent
Tano et al.

(10) Patent No.: US 6,657,071 B1
(45) Date of Patent: Dec. 2, 2003

(54) PROCESS FOR PRODUCING α-SULFO-FATTY ACID ALKYL ESTER SALT

(75) Inventors: Tetsuo Tano, Tokyo (JP); Masahisa Yoshiya, Tokyo (JP); Taku Nishio, Tokyo (JP); Seiji Matoba, Tokyo (JP); Yozo Miyawaki, Tokyo (JP)

(73) Assignee: Lion Corporation, Tokyo (JP)

( * ) Notice: Subject to any disclaimer, the term of this patent is extended or adjusted under 35 U.S.C. 154(b) by 146 days.

(21) Appl. No.: 10/018,578

(22) PCT Filed: Jun. 23, 2000

(86) PCT No.: PCT/JP00/04131

§ 371 (c)(1),
(2), (4) Date: Dec. 13, 2001

(87) PCT Pub. No.: WO01/00572

PCT Pub. Date: Jan. 4, 2001

(30) Foreign Application Priority Data

Jun. 25, 1999 (JP) ............................................. 11-180946

(51) Int. Cl.⁷ .................................................. C11D 1/28

(52) U.S. Cl. .............................. 554/97; 554/85; 554/88; 554/96

(58) Field of Search ............................. 584/86, 88, 96, 584/47

(56) References Cited

FOREIGN PATENT DOCUMENTS

| EP | 644185 | * | 3/1995 | |
|---|---|---|---|---|
| EP | 644185 A1 | | 3/1995 | ......... C07C/309/17 |
| JP | 7-197080 A | | 8/1995 | ............ C11D/1/28 |
| JP | 8-81694 A | | 3/1996 | ............ C11D/1/28 |
| JP | 09-216863 | * | 8/1997 | |
| JP | 9-216863 A | | 8/1997 | ......... C07C/309/17 |
| JP | 10-182590 | * | 7/1998 | |
| JP | 10-182590 A | | 7/1998 | ......... C07C/309/17 |
| JP | 2000-191626 | | 4/2000 | ......... C07C/303/06 |
| JP | 200-128855 | | 5/2000 | ......... C07C/309/17 |
| JP | 2000-128852 | | 5/2000 | ......... C07C/303/06 |

* cited by examiner

Primary Examiner—Deborah D. Carr
(74) Attorney, Agent, or Firm—Darby & Darby

(57) ABSTRACT

By conducting a sulfonation step for bringing a fatty acid alkyl ester into contact with a sulfonating gas in the presence of a coloring inhibitor to sulfonate the fatty acid alkyl ester, an esterification step for esterifying the product of the sulfonation step with a lower alcohol, a neutralization step for neutralizing the esterified product of the esterification step to obtain a neutralized product, a bleaching step for bleaching the neutralized product to obtain a bleached product, and preferably an optional deodorization step for deodorizing the bleached product, the production process can be simplified and α-sulfofatty acid alkyl ester salts which have a pale color close to white and preferably have less odor can be obtained.

3 Claims, 10 Drawing Sheets

PROCESS FOR PRODUCING α-SULFO-FATTY ACID ALKYL ESTER SALT

This application is a 371 of PCT/JP00/04131 filed Jun. 3, 2000.

TECHNICAL FIELD

The present invention relates to a method for producing α-sulfofatty acid alkyl ester salts which can produce α-sulfofatty acid alkyl ester salts having a pale color close to white and preferably having less odor by a simple production process.

BACKGROUND ART

α-Sulfofatty acid alkyl ester salts are used as surfactants, have a high cleaning power, have excellent biodegradability and have less adverse effects on the environment so that their ability as materials for detergents is highly appreciated. α-Sulfofatty acid alkyl ester salts (hereinafter, sometimes referred to as α-SF) are obtained by bringing fatty acid alkyl esters into contact with a sulfonating gas to sulfonate them to produce α-sulfofatty acid alkyl esters and then neutralizing them.

FIG. 10 is a flowchart illustrating an example of the conventional production process for α-sulfofatty acid alkyl ester salts.

In this example, the step of sulfonating raw material fatty acid alkyl esters, for example, comprises the step of introducing a sulfonating gas to bring about contact therewith and the aging step of holding them at a predetermined temperature for a predetermined time.

That is, when bringing a raw material into contact with a sulfonating gas, first the reaction to insert $SO_3$ into the alkoxy group takes place to produce an $SO_3$-mono-adduct, which further reacts with $SO_3$, introducing a sulfonic group at the α-position to produce an $SO_3$-di-adduct and finally the $SO_3$ inserted to the alkoxy group is eliminated to produce α-sulfofatty acid alkyl ester, as shown in the following general formula (I).

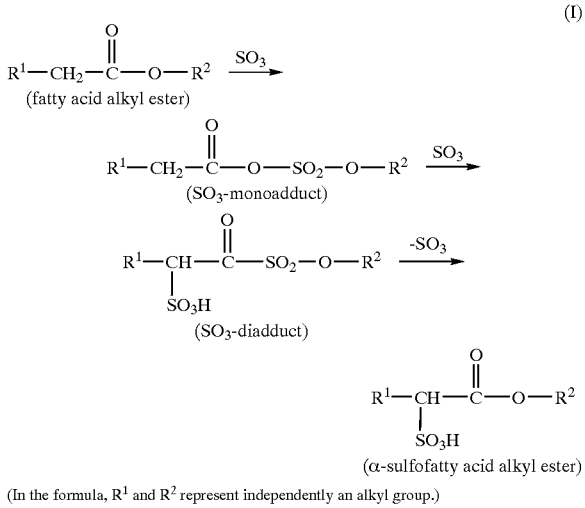

(In the formula, $R^1$ and $R^2$ represent independently an alkyl group.)

The sulfonating gas and raw material react in equimolar ratios theoretically. However, actually, the reaction is a gas-liquid reaction and since the reaction is a consecutive reaction, the sulfonating gas is used in excess of the equimolar amount. In this example, a sulfonating gas containing $SO_3$ in a molar amount of, for example, 1.2-fold as compared with the raw material is used.

Then, since the reaction is a consecutive reaction as stated above, the reaction mixture after contact with the sulfonating gas contains a mono-adduct, a di-adduct, unused fatty acid alkyl ester, and other by-products.

For this reason, in the subsequent aging step, the elimination of $SO_3$ from the di-adducts is promoted to finally attain an equilibrium state. Thus, in the sulfonated product that reaches the equilibrium state in the aging step, there exist di-adducts in an amount corresponding to the excessive mole number of $SO_3$ at least relative to the raw material.

Neutralization of the di-adducts gives rise to α-sulfofatty acid alkyl ester di-alkali salts which would not contribute to the washing effect, so that for detergent applications, it is necessary to reduce the content of the di-aduct as far as possible.

Hence, after the aging step, a lower alcohol is added to convert the di-adduct to an α-sulfofatty acid alkyl ester according to the reaction shown by the general formula (II). As will be understood from the formula, since an α-sulfofatty acid alkyl ester is produced from a di-adduct, this treatment is called an esterification step.

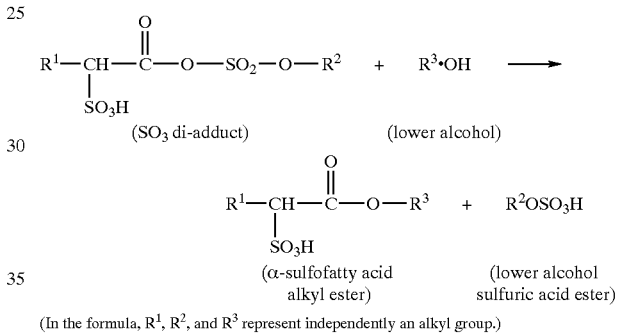

(In the formula, $R^1$, $R^2$, and $R^3$ represent independently an alkyl group.)

In the sulfonation of a fatty acid alkyl ester, the α-sulfofatty acid alkyl ester becomes colored, so that it is necessary to conduct a bleaching treatment. As illustrated in FIG. 10, the bleaching treatment is performed simultaneously with the esterification step by the addition of a bleaching agent such as an aqueous hydrogen peroxide solution together with the lower alcohol (hereinafter, the simultaneous esterification and bleaching step will be described).

In this case, theoretically, an equimolar amount of the lower alcohol reacts with the di-adduct in the sulfonated product. However, due to the side reaction by the action of the bleaching agent, the lower alcohol is consumed in an amount more than is used in the esterification. As a result, in this example, where methanol is used as the lower alcohol, methanol is used in an excess amount such as 30% by weight with respect to the sum of the α-sulfofatty acid alkyl ester and the di-adduct (hereinafter, sometimes referred to as "sulfonic acid," or simply "acid").

Also, in this example, 3% by weight of hydrogen peroxide is used in terms of pure compound with respect to the sulfonic acid.

Subsequently, the sulfonated product after the esterification and bleaching is neutralized with an aqueous alkali solution to obtain a neutralized product (α-sulfofatty acid alkyl ester salt).

In this example, the concentration of the aqueous alkali solution is 20% by weight and the neutralized product is obtained as an aqueous slurry having an activator (AI) concentration of about 50% by weight. The AI (active ingredient, i.e., activator) is the sum of the α-sulfofatty acid alkyl ester salt and α-sulfofatty acid di-alkali salt.

Incidentally, the viscosity of an aqueous slurry of an anionic surfactant shows a unique behavior such that it increases proportionally with increases in the activator concentration in the range where the activator concentration is low but it decreases in a specified concentration range when the activator concentration increases to some extent and then it increases again when the concentration becomes higher than the specified concentration range. As a result, from the viewpoints of production efficiency and reduction in viscosity, it is preferable that the above neutralized product be adjusted to have an activator concentration (AI concentration) of 60 to 80% by weight where low viscosity is shown. To this end, the concentration of the aqueous alkali solution used is high enough to achieve such an AI concentration.

On this occasion, the presence of a lower alcohol can prevent the production of by-products such as α-sulfofatty acid di-alkali salts by the following two actions.

That is, the viscosity of the above neutralized product can be further reduced by means of the lower alcohol, and the generation of by-products due to localized heating caused by the neutralization heat can be prevented. This is particularly effective where high concentration aqueous alkali solutions are used since in such cases side reactions tend to occur.

The presence of a lower alcohol also prevents generation of an α-sulfofatty acid, which is a precursor of the α-sulfofatty acid di-alkali salt, from the α-sulfofatty acid alkyl ester by a reversible reaction in the above general formula (II).

To this end, in the neutralization step, a certain excess amount of lower alcohol is needed.

Therefore, the neutralized product contains an excess amount of lower alcohol. This makes it necessary to concentrate the above neutralized product to recover the lower alcohol, purify it remove water and recycle it to the esterification step as described above. The water separated from the lower alcohol by the purification is subjected to waste water treatment and then disposed of.

In this manner, the neutralized product now free of the lower alcohol is further formed into powder, particles, etc. by conventional methods to obtain commercial products.

On the other hand, α-sulfofatty acid alkyl ester salts usually give perceptible odors so that in the case of detergent compositions in which α-sulfofatty acid alkyl ester salts are blended, and formulations which improve the odor, for example, by masking with a perfume are used.

In addition, Japanese Patent Application First Publication No. Hei 08-081694 discloses that odors can be improved by use of fatty alkyl esters having an iodine value of 2 or less and a carotenoid content of 10 ppm or less as raw materials. Also, Japanese Patent Application First Publication No. Hei 07-197080 discloses that odors can be improved by blending zeolite in detergent compositions.

However, the above-described conventional production methods have the problem that excessive lower alcohols are used therein and hence, it is necessary to recover, purify and recycle the lower alcohols from the viewpoint of cost reduction, etc., which makes the production process complicated. Also, there is the problem that the bleaching treatment alone gives insufficient color improving effects.

In the improvement of odors, the problem arises that the formulation of detergent compositions is limited and the production process is made complicated by the use of treatments such as the distillation of raw materials, hydrogenation, solvent extraction, centrifugation, etc.

Therefore, an object of the present invention is to provide a method for producing α-sulfofatty acid alkyl ester salts which includes a more simplified production process than conventional method.

More specifically, it is an object of the present invention to provide a method for α-sulfofatty acid alkyl ester salts which requires no recovery, purification or recycling of lower alcohols.

Further, it is an object of the present invention to provide a method for α-sulfofatty acid alkyl ester salts which can improve the color of the α-sulfofatty acid alkyl ester salts.

Furthermore, it is an object of the present invention to provide a method for α-sulfofatty acid alkyl ester salts which can improve the odor of the α-sulfofatty acid alkyl ester salts.

DISCLOSURE OF THE INVENTION

The method for α-sulfofatty acid alkyl ester salts according to the present invention comprises a sulfonation step for bringing a fatty acid alkyl ester into contact with a sulfonating gas in the presence of a coloring inhibitor to sulfonate the fatty acid alkyl ester, an esterification step for esterifying the product of the sulfonation step with a lower alcohol, a neutralization step for neutralizing the esterified product of the esterification step to obtain a neutralized product, and a bleaching step for bleaching the neutralized product to obtain a bleached product.

In the method for α-sulfofatty acid alkyl ester salts, it is preferable that a deodorization step for deodorizing the bleached product be conducted.

Further, in the above deodorization step, it is preferable that the bleached product be deodorized by a flush method.

BEST MODE FOR CARRYING OUT THE INVENTION

Figure 1:
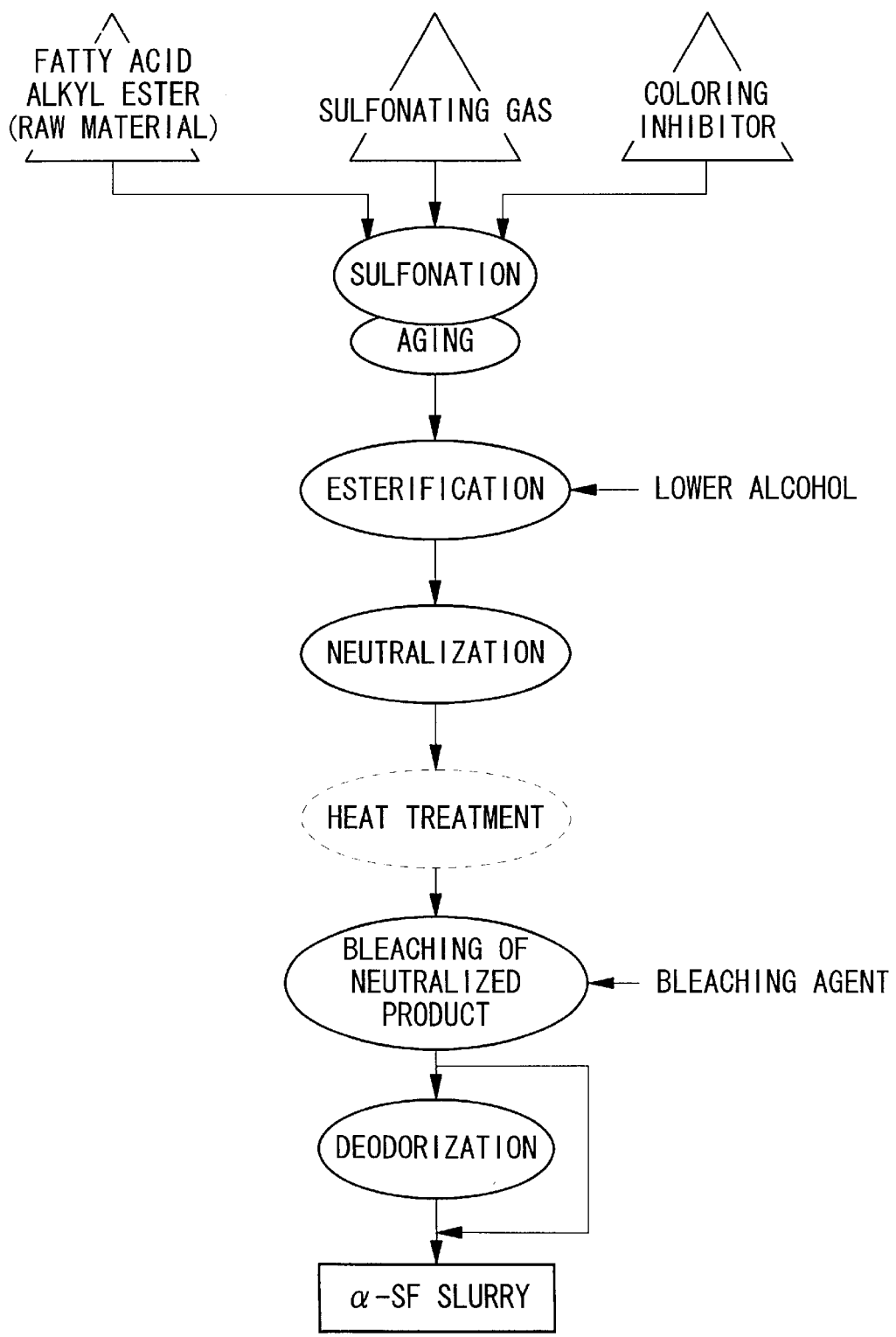
FIG. 1 is a flowchart illustrating an example of the production process for α-sulfofatty acid alkyl ester salts according to the present invention.
Figure 2:
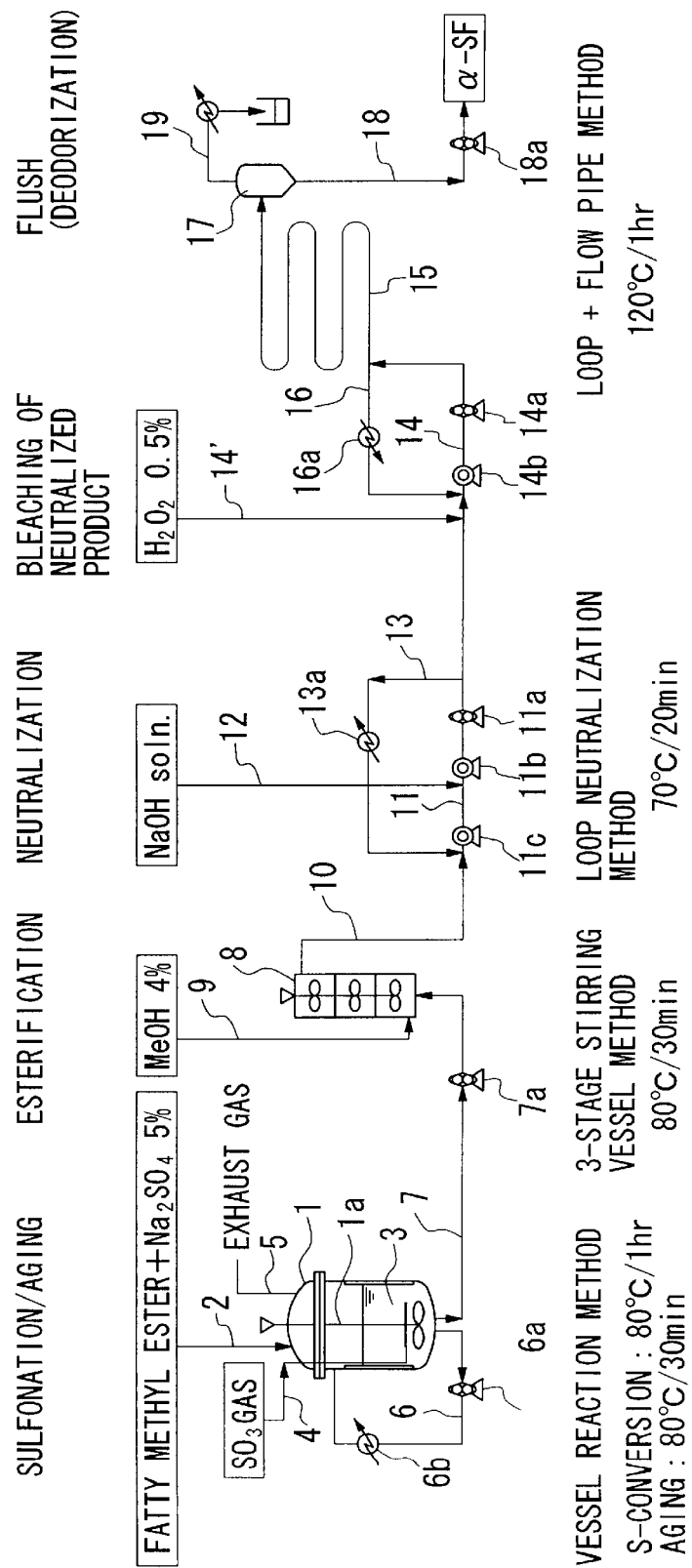
FIG. 2 is a schematic construction diagram showing a production apparatus used in the production method for α-sulfofatty acid alkyl ester salts according to the present invention.

FIG. 1 is a flowchart illustrating an example of the production process for α-sulfofatty acid alkyl ester salts according to the present invention and FIG. 2 is a schematic construction diagram of the production apparatus.

In FIG. 2, the conditions are shown for a case in which a fatty acid methyl ester is used as the raw material fatty acid alkyl ester, $SO_3$ gas diluted with desiccated air is used as the sulfonating gas, $Na_2SO_4$ (Glauber's salt) is used as the coloring inhibitor, methanol is used as the lower alcohol, an aqueous NaOH solution is used as the aqueous alkali solution, and $H_2O_2$ (hydrogen peroxide) is used as the bleaching agent. All the %'s described in FIG. 2 are % by weight and it is meant that Glauber's salt is used in an amount of 5% by weight with respect to the raw material, methanol is used in an amount of 4% by weight with respect to the sulfonic acid, and hydrogen peroxide is used in an amount of 0.5% by weight as pure compound with respect to the AI.

Hereinafter, explanation will be made in accordance with the production operation for α-sulfofatty acid alkyl ester salts.

First, a fatty acid alkyl ester as the raw material, and a coloring inhibitor are charged via a raw material feed line 2 into a vessel-type reactor 1.

In the present invention, it is preferable to use a fatty acid alkyl ester of the following general formula (III)

$$R^1CH^2COOR^2 \quad\quad (III)$$

(wherein $R^1$ represents a straight or branched alkyl or alkenyl group having 6 to 24 carbon atoms and $R^2$ represents a straight or branched alkyl group having 1 to 6 carbon atoms).

The fatty acid alkyl ester is not particularly limited and may be any one of animal based oils and fats derived from beef tallow, fish oil, lanolin, etc.; plant based oils and fats derived from coconut oil, palmoil, soybeanoil, etc.; synthetic fatty acid alkyl esters derived from α-olefins by means of using an oxo-synthesis method.

Specific examples of the fatty acid alkyl ester include methyl, ethyl or propyl laurates; methyl, ethyl or propyl myristates; methyl, ethyl or propyl palmitates; methyl, ethyl or propyl stearates; methyl, ethyl or propyl esters of hardened beef tallow fatty acid; methyl, ethyl or propyl esters of hardened fish oils and fats fatty acids; methyl, ethyl or propyl esters of coconut oils and fats; methyl, ethyl or propyl esters of palm oils and fats fatty acid acids; methyl, ethyl or propyl esters of palm nut oils and fats fatty acids; etc. These may be used singly or as mixtures of two or more of them. The lower the iodine value thereof, the more desirable they are in view of both color and odor and it is preferably 0.5 or less, and more preferably 0.2 or less. In particular those having an iodine value of 0.2 or less have a great effect in improving the color as compared with those having an iodine value exceeding 0.2.

As the coloring inhibitor, inorganic sulfuric acid salts or organic acid salts containing monovalent metal ions and having a mean particle diameter of 250 μm or less are preferable. The inorganic sulfuric acid salts are not particularly limited as far as they are powdery anhydrous salts containing monovalent metal ions. For example, sodium sulfate, potassium sulfate, lithium sulfate, etc. are exemplified. The mean particle diameter of the inorganic sulfuric acid salts is 250 μm or less, and preferably 100 μm or less. By setting it to 250 μm or less, the contact area with the raw material becomes greater to increase their dispersibility. The inorganic sulfuric acid salts have high coloring inhibition effects and are mostly inexpensive and further are components which can be blended with detergents so that they do not have to be finally removed from the α-sulfofatty acid alkyl ester salts (commercial products).

As the organic acid salts, sodium formate, potassium formate, sodium acetate, etc. are preferable. The mean particle diameter of the organic acid salts is also set to 250 μm or less, preferably 100 μm or less from the viewpoint of an increased contact area with the raw material.

The addition amount of the coloring inhibitor is 0.1 to 30% by weight, preferably 0.1 to 20% by weight, more preferably 2 to 20% by weight based on the raw material fatty acid alkyl ester. If it is below 0.1% by weight, the effect of addition cannot be obtained.

Although a vessel-type reactor 1 is used in this example, the reaction method is not particularly limited and in addition to methods of film reaction, pipe-type gas-liquid mixed flow reaction, etc. may also be used. The sulfonation method is not particularly limited and a thin film sulfonation method, a batch sulfonation method, etc. can be employed.

Since it is preferred that the contact with the sulfonating gas be conducted in a state where the coloring inhibitor is dispersed in the raw material as uniformly as possible, a vessel reaction method is preferable particularly in a batch sulfonation method.

Then, while stirring with a stirrer 1a, the internal temperature of the vessel-type reactor 1 is elevated to a predetermined reaction temperature to form a solid-liquid mixed phase 3 in which the coloring inhibitor particles are dispersed in the liquid raw material.

The above reaction temperature is set to a temperature at which the fatty acid alkyl ester has flowability. Generally, it is no lower than the melting point of the fatty acid alkyl ester, and preferably from the melting point to a temperature 70° C. higher than the melting point. The upper limit of the reaction temperature is set to 150° C. At temperatures above 150° C., sometimes coloring tends to occur.

Subsequently, a sulfonating gas is introduced through a gas introduction pipe 4 and brought into contact with the solid-liquid phase 3. On this occasion, an exhaust gas is exhausted from a gas exhaust outlet 5. In order to prevent an excessive increase in the reaction temperature due to contact of the raw material with the sulfonating gas which generates heat, a portion of the solid-liquid phase 3 is extracted from a circulation line 6 provided on the bottom of the vessel-type reactor 1 and again returned to the vessel-type reactor 1 at the upper part thereof for circulation by the action of a feed pump 6a and cooled after cooling it by a heat exchanger 6b.

As the sulfonating gas, $SO_3$ gas, fuming sulfuric acid, etc. can be exemplified. Preferably, $SO_3$ gas is used. $SO_3$ gas diluted with an inert gas such as desiccated air or nitrogen to a concentration of 1 to 30% by volume is preferred.

$SO_3$ is used in a molar amount of 1.0 to 2.0-fold, preferably 1.0 to 1.7-fold and since a gas-liquid reaction is involved and the reaction is not uniform, more preferably 1.05 to 1.5-fold. A molar amount of below 1.0-fold, with which the sulfonation reaction will proceed insufficiently, and a molar amount of above 2.0-fold, with which the sulfonation reaction will be vigorous so that coloring due to local heat tends to occur, are disadvantageous.

The reaction temperature varies depending on the sulfonation method. For example, it is 5 to 180 seconds, preferably 5 to 60 seconds, in the case of thin film sulfonation methods and about 10 to 120 minutes in the case of batch sulfonation methods.

In the example of conditions shown in FIG. 2, the conditions under which the sulfonation gas is contacted (described S-conversion) are 80° C. for 1 hour. The sulfonation gas is set to a molar amount of 1.2-fold.

Figure 3:
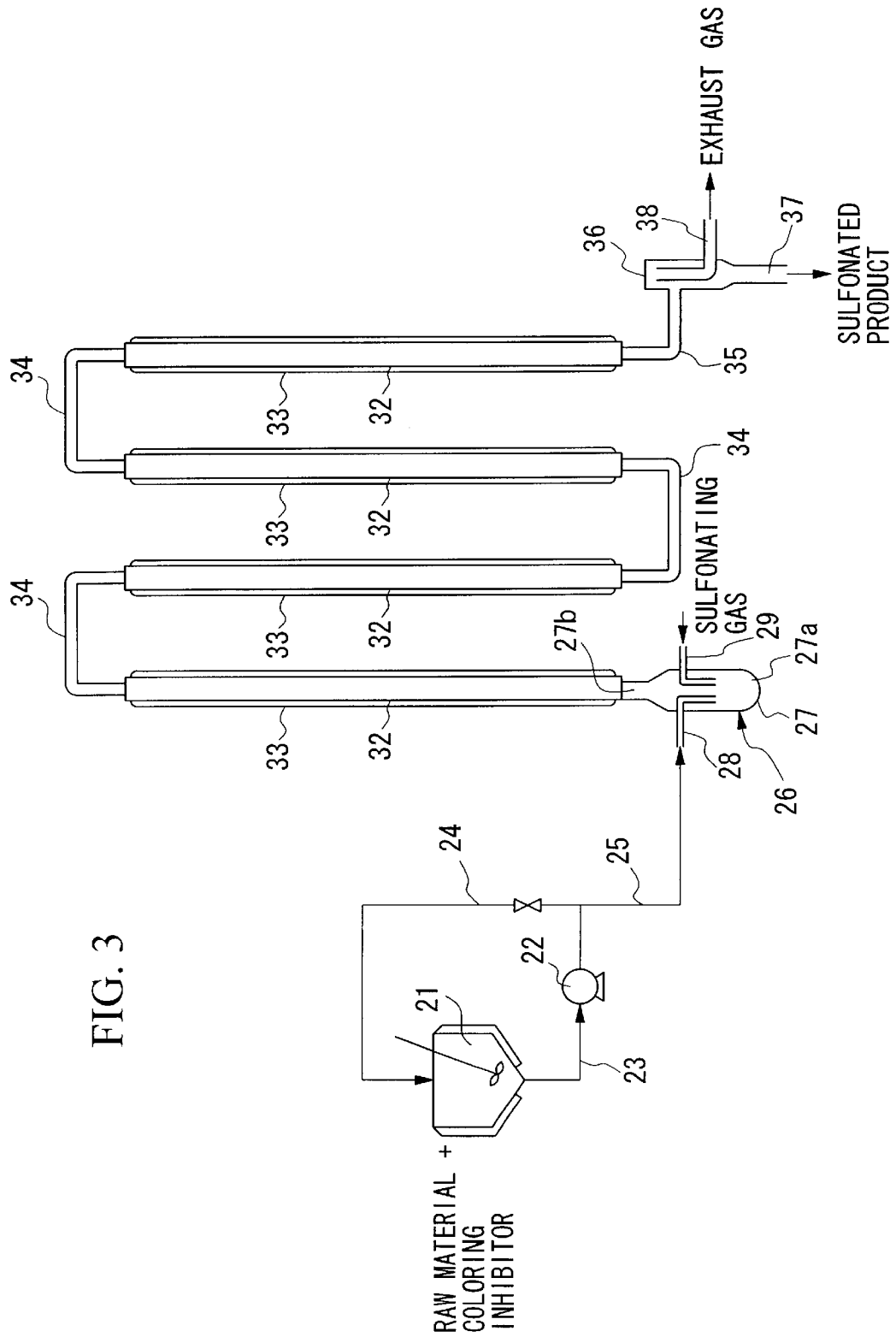
FIG. 3 is a schematic construction diagram showing an example of a reaction apparatus for conducting a pipe-type gas-liquid mixed phase flow reaction (pseudo-film reaction method).

When using a sulfonation apparatus which conducts a pipe-type gas-liquid mixed phase flow reaction (hereinafter, sometimes referred to as a pseudo-film reaction) as shown in FIG. 3, instead of the vessel-type reactor 1, a solid-liquid mixed phase in which the coloring inhibitor particles are dispersed substantially uniformly can be made in the form of a film before being brought into contact with the sulfonating gas.

That is, the raw material fatty acid alkyl ester and coloring inhibitor particles are charged into a stirring vessel 21, heated to a predetermined temperature and made a solid-liquid mixed phase in which the coloring inhibitor particles are dispersed uniformly by stirring.

Then, the above solid-liquid mixed phase is extracted through an extraction pipe 23 provided on the bottom of the stirring vessel 21 and a portion thereof is returned again to the stirring vessel 21 at the upper part thereof through a circulation pipe 24 and the remainder is fed to a raw material introduction pipe 28 provided at an introduction part 26 through a feed pipe 25. On this occasion, sulfonating gas is simultaneously introduced into the introduction part 26 through a sulfonating gas introduction pipe 29.

The diagrammatic construction of the introduction part 26 comprises an approximately tubular body 27 with its upper part being open and having a raw material introduction pipe 28 and a sulfonating gas introduction pipe 29 provided on its side surface. The opening on the upper part of the body 27 (an outlet 27b) is in the form of a circular tube and connected to the lower end of a reaction pipe 32 arranged with its axial direction being in the perpendicular direction and opening into the reaction pipe 32.

The raw material introduction pipe 28 and the sulfonating gas introduction pipe 29 are each bent in a dog-legged state so that the solid-liquid mixed phase or sulfonating gas introduced in the horizontal direction can be led in the perpendicular direction (in the descending direction) toward a bottom surface 27a in the body 27. In addition, the solid-liquid mixed phase and sulfonating gas fed into the body 27 through the raw material introduction pipe 28 and the sulfonating gas introduction pipe 29, respectively, as described above impinge against the bottom surface 27a and are mixed instantaneously and at the same time reversed upward and fed to the reaction pipe 32 through the outlet 27b above the body 27.

On the other hand, a plurality of reaction pipes 32 are arranged in parallel and connected to each other through connection pipes 34. Around each reaction pipe 32, a jacket 33 is provided, through which warm water or oil flows so that the temperature inside the reaction pipe 32 can be maintained at a predetermined reaction temperature.

The solid-liquid mixed phase fed to the reaction pipe 32 through the introduction part 26 is accelerated by the ascent of the sulfonating gas being simultaneously fed and pushed against the inner wall of the reaction pipe 32 by a large amount of sulfonating gas and as a result it ascends as a circular liquid film along the inner wall of the reaction pipe 32 and is sulfonated upon contact with the sulfonating gas.

Then, the sulfonated product and exhaust gas having passed through the final reaction pipe 32 are introduced into a recovering part 36 through a recovering part introduction pipe 35 and recovered through a sulfonated product discharging pipe 37 and an exhaust gas discharging pipe 38, respectively.

Subsequently, the predetermined temperature is maintained to conduct an aging step. In the case of the vessel-type reactor 1 shown in FIG. 2, the raw material and sulfonating gas are brought in contact with each other and then subjected to aging in the vessel-type reactor 1 while stirring the stirrer 1a. In the case of a film reaction, a pipe-type gas-liquid mixed phase flow reaction, etc., the reaction mixture is transferred to another vessel-type reactor before the aging step is performed.

The temperature of the aging step is suitably 70 to 100° C. If it is lower than 70° C., the reaction will not proceed quickly and if it exceeds 100° C., sometimes coloring tends to occur. The reaction time is set to 1 to 120 minutes.

In the example of conditions shown in FIG. 2, the aging conditions are 80° C. for 30 minutes. The aging step may be omitted depending on the reaction conditions upon contact with the sulfonating gas.

After completion of the aging step, the sulfonated product is extracted through the extraction pipe 7 provided at the bottom of the vessel-type reactor 1 by the action of the pump 7a and fed to the esterification reaction vessel 8. In this example, the esterification reaction vessel 8 is of a 3-stage stirring vessel type. In the esterification reaction vessel 8, the esterification step is carried out with a lower alcohol, which is fed through the lower alcohol feed line 9.

The lower alcohol used in the esterification step is preferably a lower alcohol having 1 to 6 carbon atoms. More preferably, a lower alcohol having the same number of carbon atoms as the number of carbon atoms of the alkyl residue of the raw material fatty acid alkyl ester is used. Theoretically, the lower alcohol undergoes equimolar reaction with the di-adduct in the sulfonated product. However, since coexistence of the lower alcohol in the neutralized product as described above results in a decrease in the viscosity of the neutralized product, the lower alcohol is added in excess so that the lower alcohol remains in an amount of 0.5 to 5% by weight relative to the AI after completion of the neutralization step.

Usually, the lower alcohol is used in a molar amount of 0.5 to 10-fold, preferably 0.8 to 5.0-fold based on the di-adduct in the sulfonated product. With a molar amount below 0.5-fold, the esterification is insufficient, while with a molar amount exceeding 10-fold, the effect will be saturation and sometimes a step for recovering the excessive lower alcohol is necessary.

The reaction temperature is 50 to 100° C., preferably 50 to 90° C. and the reaction time is set to 5 to 120 minutes.

In the example of conditions shown in FIG. 2, the di-adduct is contained in the sulfonated product in an amount of about 20% by weight and the lower alcohol (methanol) is used in an amount of 4% by weight based on the sulfonic acid. The esterification conditions are 80° C. for 30 minutes.

Subsequently, the sulfonated product extracted from the esterification vessel 8 through the extraction line 10 is fed to a neutralization line 11 by the action of a recycling pump 11a.

On the other hand, the neutralization line 11 branches a circulation line 13 after the premixer 11c, the neutralization mixer 11b, and the feed pump 11a. A portion of the neutralized product (preliminarily neutralized product) is cooled by passing through a heat exchanger 13a part way along the circulation line 13 and is thereafter fed in ahead of the premixer 11c to form a circulating loop (loop neutralization method). Between the premixer 11c and the neutralization mixer 11b, an aqueous alkali solution is fed from an alkali feed line 12.

That is, the neutralized product which circulates through the circulation line 13 is sufficiently mixed with the sulfonated product fed from the extraction line 10 by the action of the premixer 11c and the resulting mixture is mixed and neutralized with the aqueous alkali solution fed from the alkali feed line 12 by the neutralization mixer 11b, in accordance with a loop neutralization method.

In this case, the AI concentration of the neutralized product is 10 to 80% by weight, preferably 60 to 80% by weight, more preferably 62 to 75% by weight. In the example of conditions shown in FIG. 2, the AI concentration is 70% by weight. In the range of 10 to 60% by weight, there is a tendency that the production efficiency is low in a lower concentration range but the viscosity of the neutralized product is low while in a higher concentration range, the viscosity of the neutralized product is high. In the range of 60 to 80% by weight, the viscosity is moderately low, which is preferable from the viewpoints of handling and production efficiency.

As the aqueous alkali solution, for example, aqueous solutions of alkali metals, alkaline earth metals, ammonia, and ethanolamine are used. The concentration of the aqueous alkali solution is about 50% by weight or less, preferably about 15 to 50% by weight. When this is less than 15% by weight, it is sometimes difficult to adjust the AI concentration of the neutralized product to be within the range of 60 to 80% by weight In this example, the concentration of the aqueous alkali solution is 34% by weight.

The neutralized product (preliminarily neutralized product) to be added to the sulfonated product is 5 to 25-fold by weight, and preferably 10 to 20-fold by weight based on the sum of the sulfonated product and the aqueous alkali solution to be added thereto. When this is below 5-fold by weight, the effect of inhibiting by-products is small, while above 20-fold by weight, the production efficiency decreases. In this example, it is set to an amount of 20-fold.

Generally, when the sulfonated product is brought into contact with a high concentration aqueous alkali solution, by-products tend to be produced by side reactions such as hydrolysis. However, when the neutralized product is circulated and mixed with the sulfonated product by the premixer 11c before neutralization can be performed as described above, an excessive reaction in the initial stage of reaction is inhibited so that the production of by-products can be inhibited.

If the production amount of the α-sulfofatty acid di-alkali salts, by-products, is large, the α-sulfofatty acid di-alkali salts will adhere mainly in the apparatus in which the neutralization reaction is performed to sometimes cause clogging of the line or the like. Once such a clogging occurs, the apparatus must be stopped and washed. Therefore, the inhibition of production of α-sulfofatty acid di-alkali salts in the neutralization step has a great effect not only from the viewpoint of improving the purity of the commercial product but also from the viewpoint of improving the production efficiency.

As described above, during the neutralization step, the viscosity of the neutralized product is further decreased due to the residue of the lower alcohol. This can inhibit by-production of the α-sulfofatty acid di-alkali salts due to the localized contact of a portion of the sulfonated product with a high concentration aqueous alkali solution in the initial stage of the reaction. Also, the presence of the lower alcohol can control the reversible reaction in the above general formula (II) to inhibit the production of by-products.

The neutralization temperature is set to 30 to 140° C., preferably 50 to 140° C., and more preferably 30 to 70° C. and the neutralization time is 10 to 60 minutes. In this example, they are set to 70° C. and 20 minutes, respectively. The neutralization step is performed preferably in a range in which the pH of the mixture of the sulfonated product, neutralized product and aqueous alkali solution is acidic or weakly alkaline (pH 4 to 9). When it is strong alkalinity, there is the possibility that the ester bonds tend to be cleaved.

The neutralization step of the present invention can be performed by reacting the sulfonic acid with solid metal carbonate or hydrogen carbonate as well as by use of the aqueous alkaline solution. In particular, neutralization with solid metal carbonate (concentrated soda ash) is inexpensive as compared with neutralization with other bases and preferable.

Neutralization performed with solid metal carbonate is advantageous since the moisture in the reaction mixture becomes less so that the neutralized product will not be strongly alkaline and heat of neutralization generated upon neutralization is lower than is generated by use of metal hydroxide.

As the metal carbonate or hydrogen carbonate, sodium carbonate, potassium carbonate, ammonium carbonate, sodium hydrogen carbonate, potassium hydrogen carbonate, ammonium hydrogen carbonate, etc. may be exemplified and anhydrates, hydrates or mixtures of these may be used.

Then, the neutralized product passed through the line 11 is fed to a bleaching agent mixing line 14 by the action of a feed pump 14a.

The bleaching agent mixing line 14 branches into a circulation line 16 after the mixer 14b and the feed pump 14a, and a portion of the neutralized product mixed with a bleaching agent is fed in before the mixer 14b after passing through a heat exchanger 16a, forming a circulating loop (loop method).

Before the feed site of the neutralized product already mixed with the bleaching agent (preliminarily bleached product), a bleaching agent from a bleaching agent feed line 14' is fed in.

That is, in the bleaching agent mixing line 14, the neutralized product is mixed with the neutralized product already mixed with the bleaching agent fed through the circulation line 16 and with the freshly added bleaching agent fed through the bleaching agent feed line 14'. As a result, an excessive reaction in the initial stage of the reaction can be inhibited so that production of by-products can be inhibited.

Since the viscosity of the neutralized product is decreased by the remaining lower alcohol as described above, in the bleaching step, side reactions due to the contact of a portion of the neutralized product with locally excessive bleaching agent particularly in the initial stage of the reaction can be inhibited. The presence of the lower alcohol can control the reversible reaction in the above general formula (II) to inhibit the production of by-products.

Subsequently, the mixture is fed to the bleaching line 15 and while it proceeds in the bleaching line 15 by a flow pipe method, bleaching reaction further proceeds to form a bleached product.

As the bleaching agent, for example, aqueous solutions of hydrogen peroxide, hyposulfurous acid salt, etc. can be used. They are used in an amount of 0.1 to 10% by weight, preferably 0.1 to 5% by weight, as pure compound based on the AI. The hydrogen peroxide concentration or hypochlorite concentration of the aqueous solutions is not particularly limited. In this example, it is set to 0.5% by weight as pure compound based on the AI.

In the present invention, the neutralized product is bleached. As a result, the neutralized product is more stable than the conventional method in which the bleaching is performed simultaneously with the esterification of the sulfonated product and no interaction with the esterification reaction will occur so that side reactions do not occur readily. Also, since the consumption amount of the bleaching agent is small, the use amount of bleaching agent is made smaller than is conventional. In this example, the addition amount of hydrogen peroxide is set to 0.5% by weight as pure compound (based on the AI).

The neutralized product already mixed with the bleaching agent (preliminarily bleached product) is mixed with non-bleached neutralized product in an amount of 5 to 30-fold by weight. If the amount is below 5-fold by weight, the inhibitory effect on by-products is small, while an amount of above 30-fold by weight decreases the production efficiency.

The bleaching temperature is 50 to 140° C., preferably 80 to 140° C. when hydrogen peroxide is used or 30 to 80° C. when hypochlorous acid is used. The sum of reaction times in the bleaching agent mixing line 14 and bleaching line 15 is about 30 to 360 minutes. In this example, they are set to 120° C. and 1 hour. The pH in the bleaching step is preferably 4 to 9.

Although not shown in the diagram of the apparatus of FIG. 2, heat treatment conducted between the neutralization step and the bleaching step using a bleaching agent can further improve the color of the commercial product.

That is, the neutralized product is heated at 80° C. or higher, preferably 80 to 170° C. and held for 0.5 hour to 7 days, preferably 1 hour to 5 days, more preferably 2 to 24 hours.

Then, the bleached product in the bleaching line 15 shown in FIG. 2 is subjected to a deodorization step, if necessary.

The deodorization method includes, for example, 1) a method of adsorption using activated carbon, zeolite, silica gel, ion exchange resin, etc.,
2) a method of chemical reaction using a catalyst, ozone, light, etc.,
3) a method of evaporating deodorant components by thin film distillation, flush, etc.,
4) a method for removing deodorant components by extraction, and the like. Among them, the flush method is particularly preferred since it is high in the effect of removing odor and simple in operation.

In the method illustrated in FIG. 2, the bleached product is heated or pressurized, if necessary, adjusted to a temperature of 100 to 150° C. and a pressure of 1.5 to 11 kg/cm$^2$, introduced into a flush can 17, and flushed under reduced pressure or normal pressure to deodorize it. In this example, it is set such that a bleached product adjusted to 120° C. and 4 kg/cm$^2$ is introduced into the flush can 17 and flushed at a normal pressure. The flush makes low boiling components, causes of odor, be selectively evaporated and removed through an exhaust line 19.

The shape of the flush can 17, specific flush method, and flush nozzles are not particularly limited. The flush may be performed by recycling or continuously in multiple stages.

More particularly, the AI concentration of the bleached product after the flush, like the AI concentration before the flush, is set so as to be maintained in the range of 60 to 80% by weight, and preferably 62 to 75% by weight. In this example, it is set up such that after the flush, an aqueous slurry having an AI concentration of 70% by weight can be obtained.

Where the AI concentration range cannot be maintained, the viscosity will increase and handling will be difficult. Preferably, when the conditions are set such that the amount of evaporation per unit weight (1 kg) of AI is about 10 to 200 g, odor can be improved with greater certainty.

If the temperature of the bleached product before introduction to the flush can 17 exceeds 150° C. or the pressure exceeds 11 kg/cm$^2$, it is sometimes the case that the amount of evaporation will be too great to maintain the preferred range of the AI concentration, or thermal deterioration of the activator will occur. If the temperature is below 100° C. or the pressure is below 1.5 kg/cm$^2$, the effect of improving odor is insufficient.

The temperature and pressure of the flush can 17, residence time in the flush can 17, etc. may be adjusted appropriately depending on the volume of the flush can 17, the volume of the bleached product to be treated, etc. Usually, the pressure in the case of reduced pressure is about 150 to 600 mmHg and the residence time is about 1 to 120 minutes.

Then, the deodorized bleached product is extracted through an extraction line 18 by the action of a feed pump 18a. If necessary, the remaining hydrogen peroxide can be subjected to reduction treatment with a reducing agent such as sodium sulfite.

Further, the bleached product is molded into powder, particle, etc. to obtain a commercial product (α-sulfofatty acid alkyl ester salts).

In FIG. 2, description is made such that a throughout continuous production is performed. However, the present process is applicable to any one of a continuous method or a method in which production is performed unit by unit separately.

As described above, the primary feature of the production process is to bleach the neutralized product.

That is, since no esterification is performed simultaneously with bleaching unlike the conventional method, in the esterification step, consumption of lower alcohol by side reactions by the action of the bleaching agent does not have to be taken into consideration. Also, in the neutralization step after the esterification step, the amount of consumption of lower alcohol can be decreased attributable to the effect of the prevention of hydrolysis.

As a result, the addition amount of lower alcohol may be adjusted such that an amount necessary for the inhibition of a decrease in viscosity and production of by-products in the neutralization step in addition to the amount necessary for esterification will remain so that it can be set to an addition amount less than is used conventionally. Therefore, the amount of the lower alcohol remaining in the commercial product is small and hence there is no need for recovery, purification and recycling of lower alcohols, enabling simplification of the production step.

Figure 10:
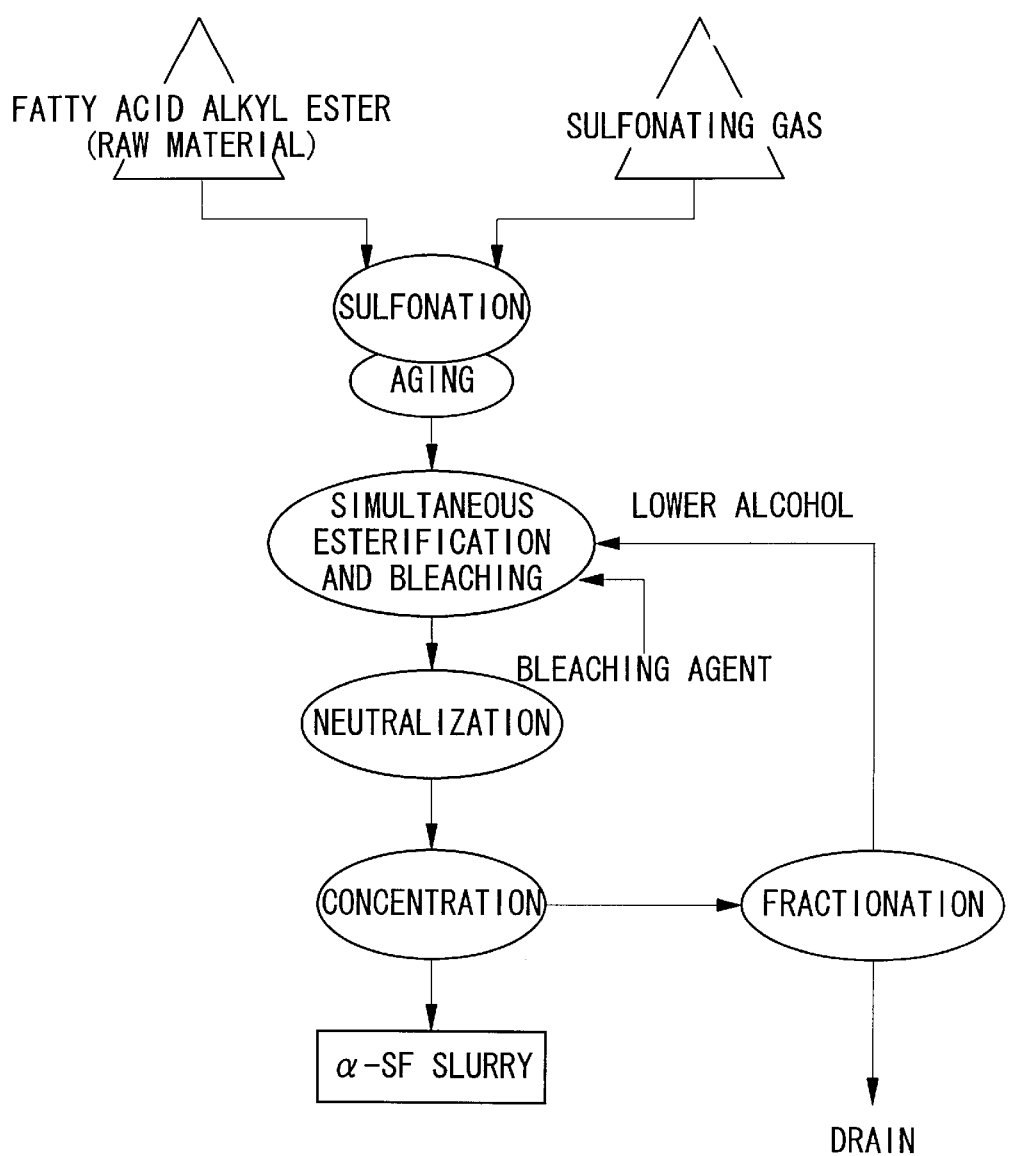
FIG. 10 is a flowchart illustrating an example of the conventional production process for α-sulfofatty acid alkyl ester salts.

More particularly, as described above, when use is made of methanol in the conventional example as illustrated in FIG. 10, in the simultaneous esterification and bleaching step, an excessive amount of methanol in as much as 30% by weight is added. On the other hand, in the example of conditions illustrated in FIGS. 1 and 2, the addition of methanol is only in the esterification step and the addition amount is 4% by weight based on the sulfonic acid. Therefore, the amount of methanol in this example is significantly reduced when compared with the conventional example illustrated in FIG. 10.

Further, sulfonation in the presence of a coloring inhibitor can give rise to α-sulfofatty acid alkyl ester salts having pale colors close to white.

Also, preferably by performing the deodorization step (preferably by a flush method under specified conditions), α-sulfofatty acid alkyl ester salts having fewer odors can be obtained.

Hereinafter, explanation will be made of results of experiments studied upon determining the example of conditions illustrated in FIG. 2.

Figure 4A:
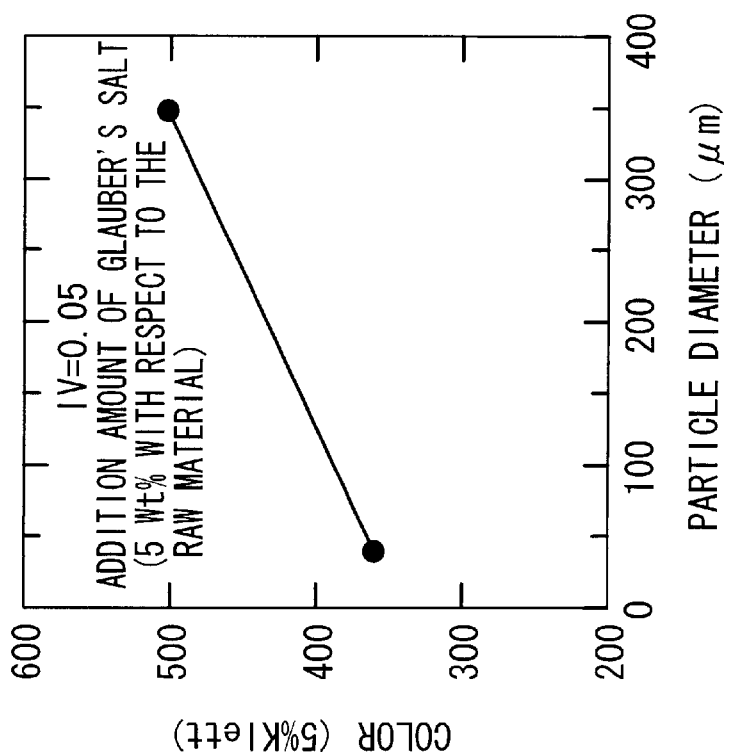
FIG. 4(a) and FIG. 4(b) are graphs illustrating an example of the relationship between the addition amount of a coloring inhibitor and color and an example of the relationship between the mean particle diameter and color, respectively.
Figure 4B:
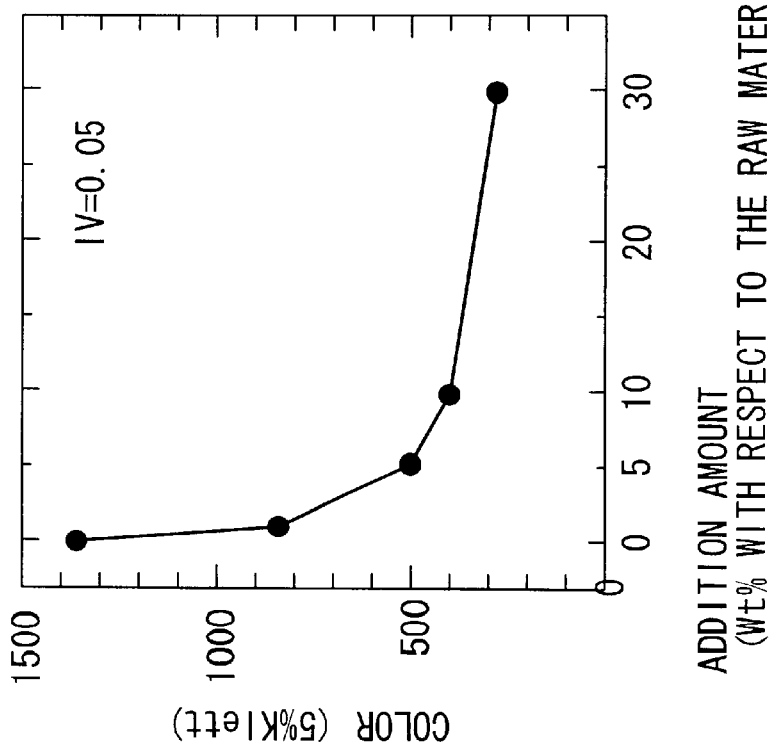

FIG. 4(a) and FIG. 4(b) are graphs illustrating an example of the relationship between the addition amount of a coloring inhibitor and color and an example of the relationship between the mean particle diameter and color, respectively.

Hereinafter, the color (or 5% Klett) shown in FIG. 4(a) to FIG. 9(b) means a value obtained by measuring 5% by weight ethanol solution or 5% by weight aqueous solution of sulfonic acid or AI on a Klett photoelectric photometer using a No. 42 Blue Filter having a light path length of 40 mm.

In this example, the coloring inhibitor is Glauber's salt and the raw material is of an iodine value (IV) of 0.05. In FIG. 4(a), Glauber's salt having a particle diameter of 40 to 50 μm is used.

From the graph in FIG. 4(a), it will be apparent that the addition of the coloring inhibitor improves the color greatly. Further, from the graph in FIG. 4(b), it can be seen that the smaller the particle size is, the greater the color improving effect is. And from these results of experiments, the addition amount of the coloring inhibitor is set to 5% by weight and it was decided to use fine powder Glauber's salt having a mean particle diameter of 40 to 50 μm.

Figure 5:
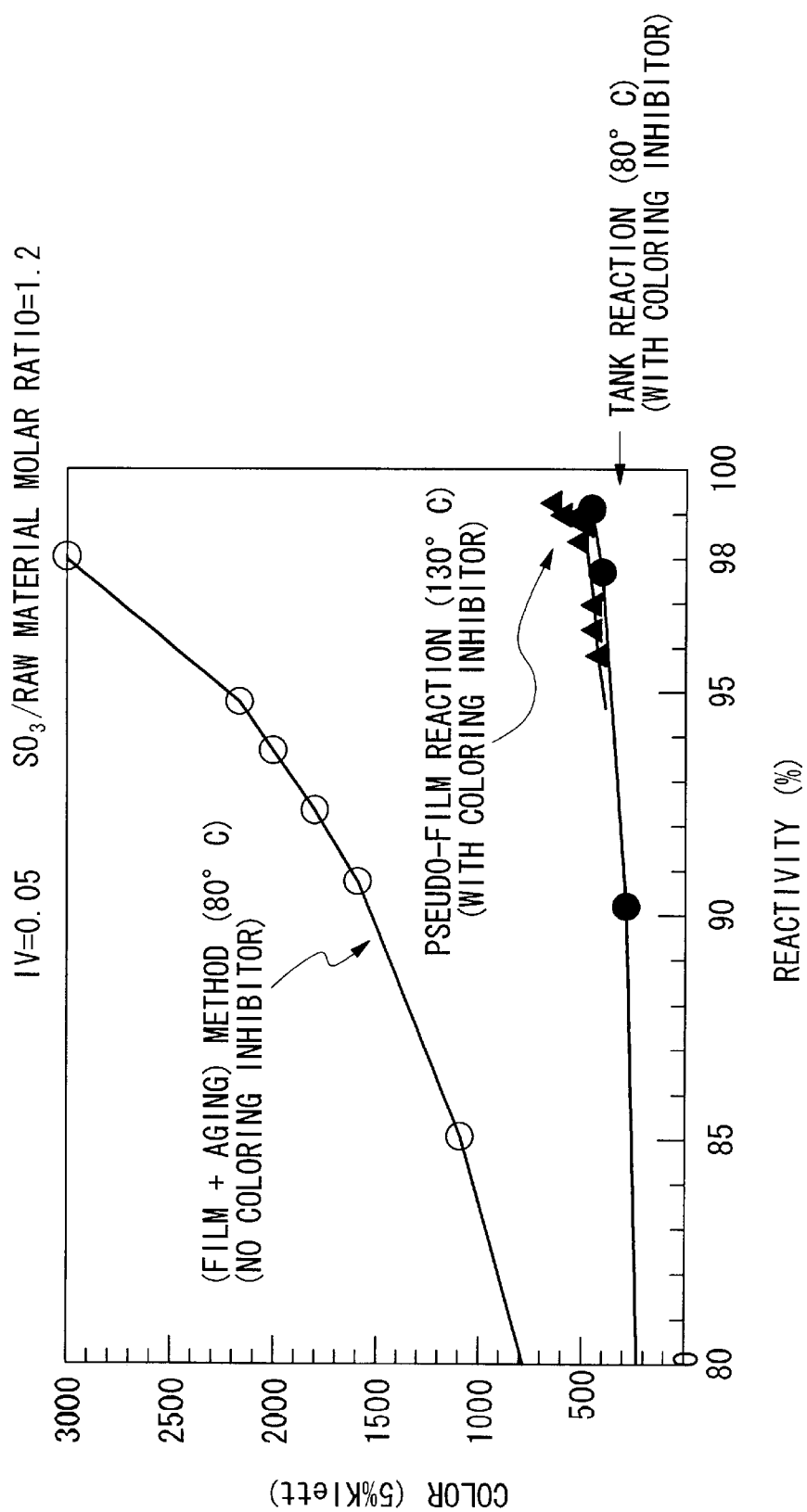
FIG. 5 is a graph illustrating the effects of the reaction method and coloring inhibitor, respectively.

FIG. 5 is a graph illustrating the effects of the reaction method and coloring inhibitor, respectively. The (film+ aging) method indicates the results of experiments obtained by contacting a fatty acid alkyl ester with a sulfonating gas by an ordinary film reaction in the absence of coloring inhibitors, and then performing aging. The vessel reaction indicates results of experiments obtained by contacting a fatty acid alkyl ester with a sulfonating gas in the presence of a coloring inhibitor (Glauber's salt) using the vessel-type reactor 1 as illustrated in FIG. 2 and subsequently performing an aging step. The pseudo-film reaction indicates the results of experiments on a pipe-type gas-liquid mixed phase flow reaction using a sulfonating apparatus illustrated in FIG. 3, conducted in the presence of a color inhibitor (Glauber's salt). In this case, since the reactivity of the sulfonated product recovered from the apparatus is sufficiently high, no aging step is performed.

From the graph, it can be confirmed that the color improving effect of the color inhibitor is great and in the sulfonating apparatus illustrated in FIG. 3, like the vessel-type reactor 1 shown in FIG. 2, the particles of the color inhibitor can be brought into contact with the sulfonating gas while they are being uniformly dispersed in the raw material.

Figure 6:
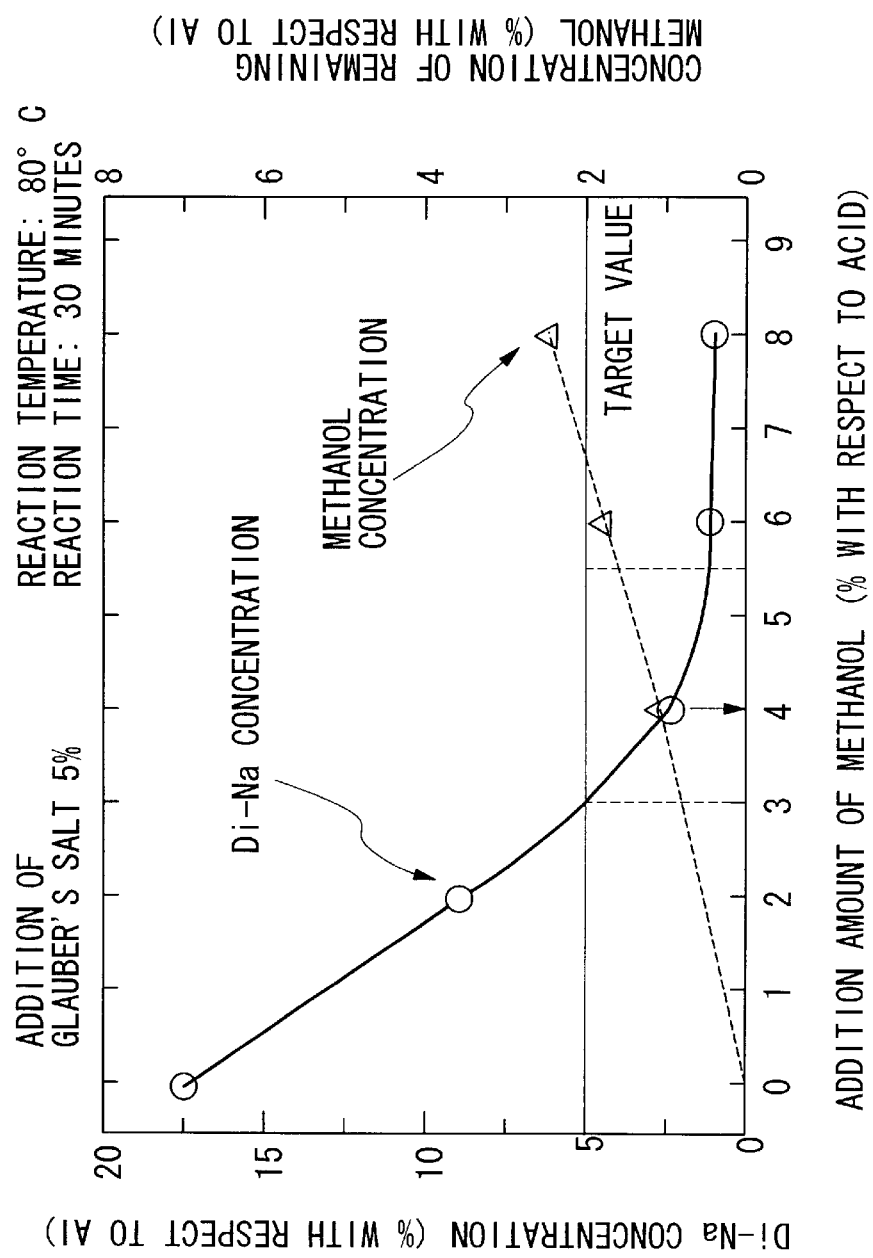
FIG. 6 is a graph illustrating the results of experiments for studying the use amount of methanol in the esterification step.

FIG. 6 is a graph illustrating the results of experiments for studying the use amount of methanol in the esterification step. The reaction temperature and reaction time are reaction temperature and reaction time, respectively, for the esterification step.

The horizontal axis stands for the addition amount of methanol vs. the sulfonic acid in the esterification step. The vertical axis stands for the concentration of α-sulfofatty acid di-sodium salts (Di—Na) in the neutralized product after neutralization after the esterification step and the concentration of remaining methanol in the neutralized product. The target values are Di—Na concentration and remaining methanol concentration after neutralizing and it is aimed at setting conditions such that a numerical range having smaller values than the specified values can be obtained.

From the graph, 4% by weight is adopted, and this value satisfies the target value as the addition amount of methanol and can give an amount of remaining methanol concentration suitable for decreasing the viscosity as described above.

Figure 7:
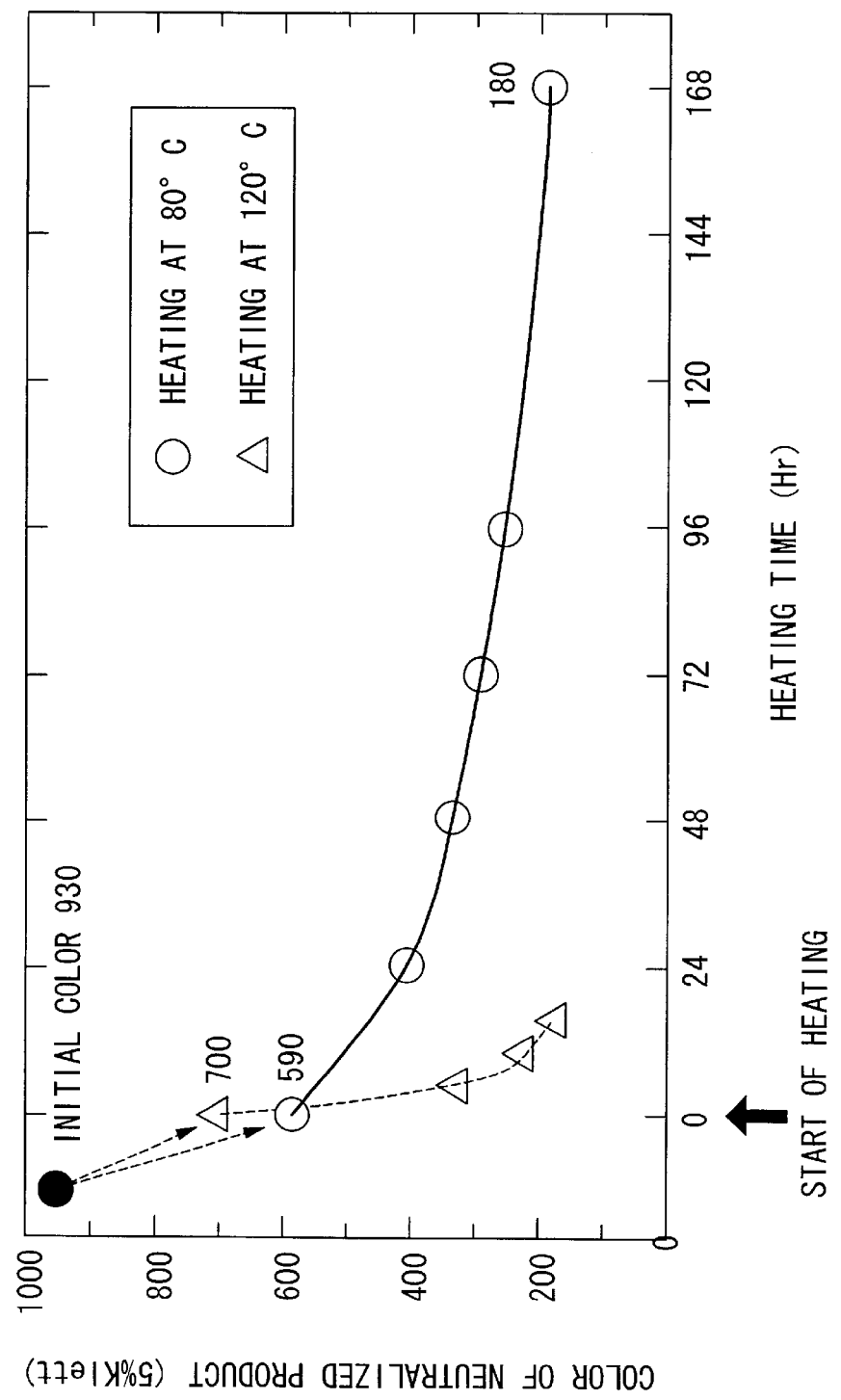
FIG. 7 is a graph illustrating the results of experiments on the effect of the heat treatment step.

FIG. 7 is a graph illustrating the results of experiments on the effect of the heat treatment step, though not conducted in the apparatus shown in FIG. 2.

As will be understood from the graph, it is apparent that the heat treatment improves the color.

Figure 8:
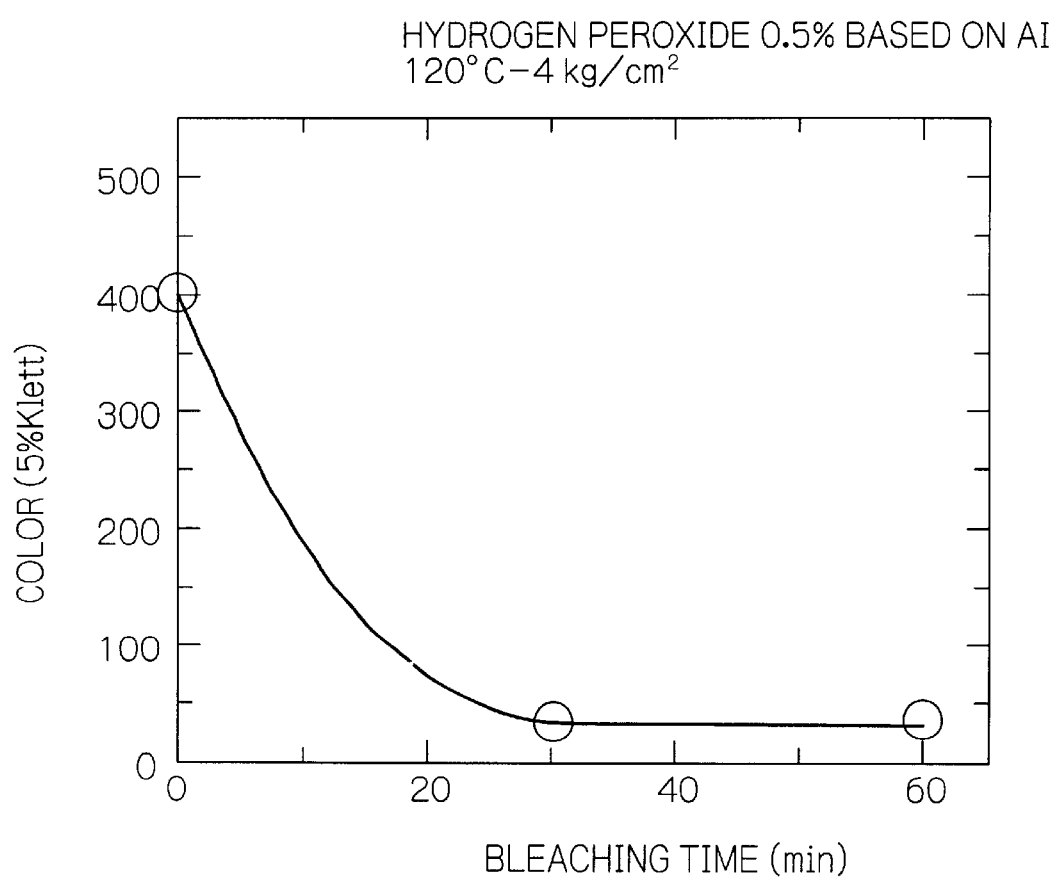
FIG. 8 is a graph illustrating the results of study on the color inhibiting effect of hydrogen peroxide.
Figure 9:
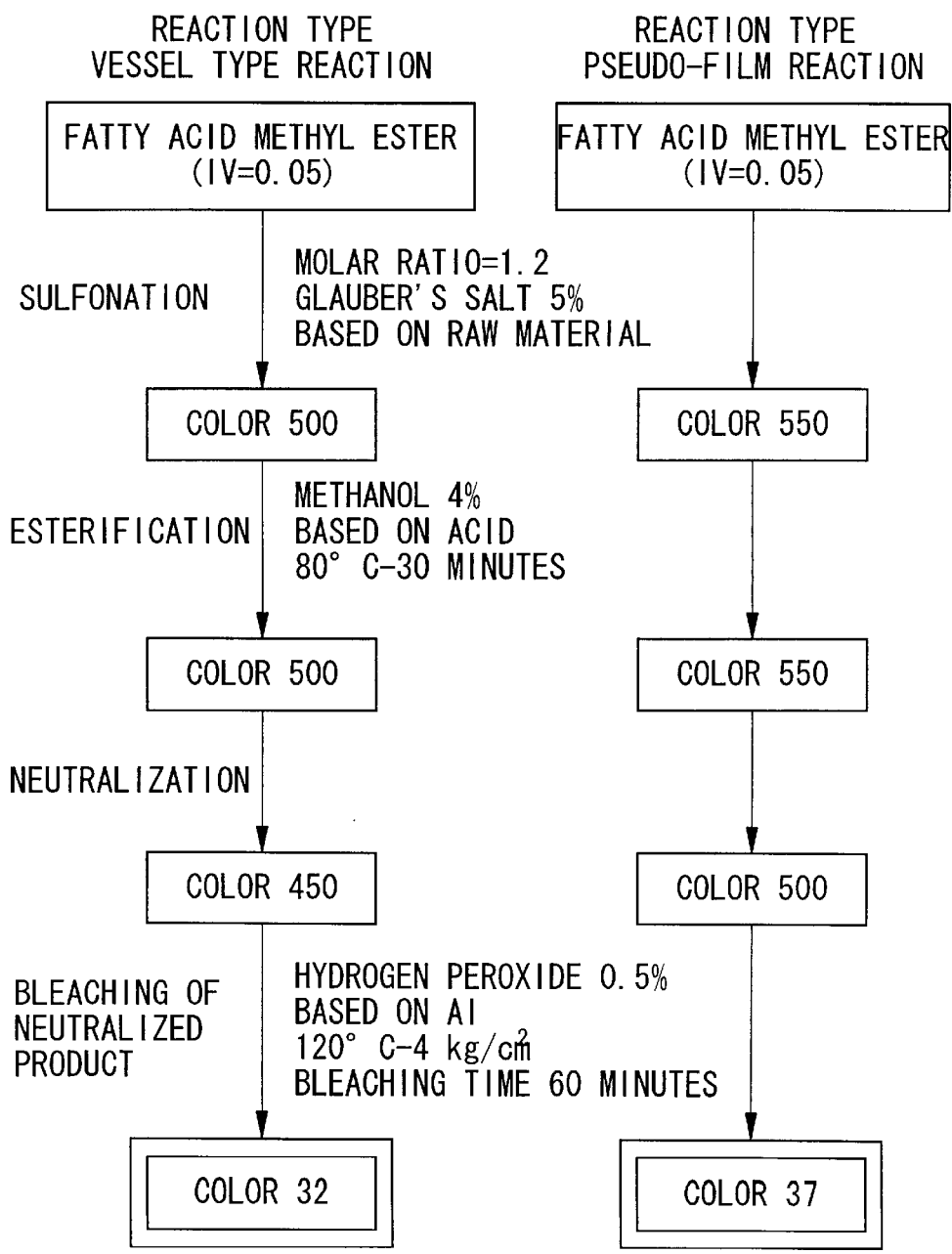
FIG. 9, consisting of FIGS. 9(a) and 9(b) which is discussed below, illustrates changes in color in each step in the experiments based on the results of the studies illustrated in FIGS. 4 to 8, FIG. 9(a) illustrating the results of the experiments using the vessel-type reactor shown in FIG. 2, and FIG. 9(b) illustrating the results of experiments using the sulfonation apparatus of the psuedo-film reaction method shown in FIG. 3.

FIG. 8 is a graph illustrating the results of study on the color inhibiting effect of hydrogen peroxide. It can be seen that in an addition amount of 0.5% as pure compound based on the AI, sufficient effects can be obtained at the temperature condition of 120° C. Notice that 4 kg/cm$^2$ is by absolute pressure.

FIG. 9(a) and FIG. 9(b) illustrate changes in color in each step in the experiments based on the results of such a study as above. FIG. 9(a) illustrates the results of experiments using the vessel-type reactor shown in FIG. 2 and FIG. 9(b) illustrates the results of experiments using a sulfonation apparatus of the pseudo-film reaction method shown in FIG. 3. In each case, however, no heat treatment is performed.

Major operations and conditions are shown in FIG. 9(a) and the same will do in FIG. 9(b). In Table 1, the composition of the obtained bleached product, the reactivity of the raw material, and measured values of color are shown.

The comparative example shown in Table 1 indicates the results of experiments of production according to the flow of the conventional method shown in FIG. 10 without using any coloring inhibitor (continuous sulfonation using a film reactor, with an aging step). That is, the α-sulfofatty acid alkyl ester salt of the comparative example is produced by sulfonation in a film reactor and aging at 80° C. for 60 minutes and then bleaching by a simultaneous esterification and bleaching method. The addition amount of methanol is 30% by weight based on the sulfonic acid and hydrogen peroxide is used in an amount of 3% by weight as pure compound based on the sulfonic acid. Further, after the neutralization step, excessive methanol is removed using a general evaporator.

TABLE 1

| Item | Pseudo-film reaction method | Vessel reaction method | Comparative example |
| --- | --- | --- | --- |
| AI (%) | 69.2 | 70.2 | 68.3 |
| Methyl sulfate (% based on AI) | 7.5 | 7.5 | 6.0 |
| Glauber's salt (% based on AI) | 2.4 | 2.3 | 2.0 |
| Di-Na (% based on AI)* | 2.6 | 2.7 | 4.7 |
| Remaining methanol (% based on AI) | 1.2 | 1.2 | 2.3 |
| Remaining hydrogen peroxide (% based on AI) | 0.05 | 0.05 | 0.12 |
| Reactivity (%) | 98.5 | 98.6 | 97.5 |
| Color (5% Klett) | 37 | 32 | 35 |

*Di-Na: α-sulfofatty acid di-Na salts

From the results in FIG. 9(a), FIG. 9(b), and Table 1, it is confirmed that a color can be obtained in good values by any one of the methods. Further, it can be seen that in the method of the present invention, as compared with the comparative example, the content of α-sulfofatty acid di-sodium salts (Di—Na) is low, giving a highly pure product.

Embodiments of the present invention will be summarized as follows.

(1) It is preferable that a heat treating step at 80° C. or higher be performed between the neutralization step and the bleaching step.
(2) As the color inhibitor, inorganic sulfuric acid salts or organic acid salts containing monovalent metal ions and having a mean particle diameter of 250 μm or less are preferable. The addition amount of the coloring inhibitor is 0.1 to 30% by weight, preferably 0.1 to 20% by weight, and more preferably 3 to 20% by weight based on the raw material fatty acid alkyl ester.
(3) In the batch sulfonation method, a vessel reaction method is preferable.
(4) The iodine value of fatty acid alkyl esters is preferably 0.5 or less.
(5) In the esterification step, it is preferable that the lower alcohol be added so that the lower alcohol remains in an amount of 0.5 to 5% by weight relative to the AI after completion of the neutralization step.
(6) The bleaching agent is used in an amount of 0.1 to 10% by weight, preferably 0.2 to 5% by weight as pure compound.
(7) It is preferable that the neutralization method and bleaching method adopt a loop method which recycles the neutralized product, neutralized product already mixed with a bleaching agent, and the bleaching agent.

EXAMPLES

Hereinafter, the present invention will be described in more detail by examples.

Example 1

In a pilot plant illustrated in FIG. 2, α-sulfofatty acid alkyl ester salts were produced.

The raw material used was fatty acid methyl esters which was obtained by mixing fatty acids methyl esters (sold under trade names: Pastel M-14, Pastel M-16, Pastel M-180 (manufactured by Lion Oleochemical Co., Ltd.)) obtained by esterifying and distillation palm nut oil, coconut oil, and palm oil, in a desired proportion and subjecting the mixture to hydrogenation treatment to decrease the iodine value hereof. This time use was made of a mixture of Pastel M-14 and Pastel M-16 in a weight ratio of 2:8.

The hydrogenation treatment was performed in accordance with a conventional method using as a hydrogenation catalyst SO-850 (trade name, manufactured by Sakai Chemical Co., Ltd.) in an amount of 0.1% by weight based on the fatty acid methyl ester under the conditions of 170° C. for 1 hour. After the hydrogenation treatment, the catalyst was removed by filtration.

The properties and carbon distribution of the raw material are shown in Table 2.

TABLE 2

|  | Composition |
|---|---|
| Chain length |  |
| C10 | 0–1% |
| C12 | 0–1% |
| C14 | 18–22% |
| C16 | 78–82% |
| C17 | 0–2% |
| C18 | 0–1% |

TABLE 2-continued

|  | Composition |
|---|---|
| Acid value | 1 or less |
| Unsaponified product | 1 or less |
| Moisture | 0.5% or less |
| Iodine value | 0.13 |
| Mean molecular weight | 264 |

As the sulfonating gas, one produced by catalytic oxidation of $SO_2$ using dry air (dew point −55° C.) was used.

As the coloring inhibitor, fine powder Glauber's salt of industrial grade (manufactured by Shikoku Kasei Co. Ltd.; particle diameter 40 to 50 μm) was used.

In the esterification, methanol of industrial grade (moisture 1,000 ppm or less) was used.

In the neutralization, 48% industrial grade caustic soda diluted with tap water was used.

In the bleaching, 35% industrial grade hydrogen peroxide was used.

Sulfonation Step

As the vessel-type reactor 1, one made of SUS 316L having a volume of 200 liters, jacket-cooled, provided with the stirrer 1a, with the reaction temperature being controlled by a circulation line 6 was used.

First, 80 kg of the raw material was charged in the vessel-type reactor 1 and while stirring well, 4 kg of fine powder Glauber's salt (particle diameter 40 to 50 μm) as the color inhibitor was introduced and uniformly dispersed to form the solid-liquid mixed phase 3. At this time, the temperature of the solid-liquid mixed phase 3 in the vessel-type reactor 1 was controlled to 80° C. through the jacket of the vessel-type reactor 1 and a heat exchanger 6b provided in the circulation line 6. The circulation amount in the circulation line 6 was set to 80 liters/min.

Subsequently, 102 m³ (1.2-fold by mole based on the raw material) of 8% by volume $SO_3$ gas diluted with desiccated air was introduced isochronously over 1 hour through the gas introduction pipe 4 with its end forming a sparger. This reaction was an exothermic reaction and the jacket temperature and the temperature of the heat exchanger 6b were controlled so that the temperature of the solid-liquid mixed phase 3 could be maintained at 80° C.

The solid-liquid mixed phase 3 after the introduction of $SO_3$ gas contained sulfuric acid, methyl sulfate, dimethyl sulfate, sulfur dioxide, and carboxylic acids as well as fatty acid methyl esters, $SO_3$ mono-adducts, $SO_3$ di-adducts, and α-sulfofatty acid alkyl esters, and Glauber's salt.

Then, aging was performed for 30 minutes while maintaining the reaction temperature at 80° C.

Esterification Step

The sulfonated product after aging was extracted from the extraction line 7 provided at the bottom of the vessel-type reactor 1 by the action of the pump 7a and fed to the esterification reactor vessel 8 at a rate of 113 kg/hr.

As the esterification reactor vessel 8, a 3-stage stirring vessel type one with jackets was used.

Methanol was fed through the lower alcohol feed line 9 at a rate of 4.5 kg/hr and esterification was performed and controlled such that methanol was 4% by weight based on the sulfonated product. The reaction temperature of esterification was 80° C. and residence time was 30 minutes.

The reaction product after completion of the esterification step contained sulfuric acid, methyl sulfate, dimethyl sulfate, sulfur dioxide, carboxylic acids, and dimethyl ether as well as fatty acid methyl esters, $SO_3$ mono-adducts, $SO_3$ di-adducts, and α-sulfofatty acid alkyl esters, Glauber's salt, and methanol.

Neutralization Step

Subsequently, the sulfonated product extracted from the esterification reactor vessel 8 was continuously fed to a neutralization line 11 through the extraction line 10 at a rate of 117 kg/hr. The neutralization method was a loop neutralization method, forming a loop circulating as described above and a 34% by weight aqueous sodium hydroxide solution was quantitatively fed between the premixer 11c and the neutralization mixer 11b at a rate of 46.6 kg/hr to neutralize continuously.

Then, after preliminarily mixing the sulfonated product with the preliminarily neutralized product by the premixer 11c, the resulting mixture was mixed with an aqueous sodium hydroxide solution to form a neutralized product. The amount of preliminarily neutralized product circulating in the loop was set to 20 times the sum of the sulfonated product and the aqueous alkali solution to be added.

The neutralization temperature was controlled to 70° C. by adjusting the temperature of water in the heat exchanger 13a in the loop circuit. The residence time of the neutralized product was 20 minutes.

Although not shown in FIG. 2, a pH control system was arranged in the circulation loop and the feed rate (feed amount) of the aqueous sodium hydroxide solution was controlled by a feed back controller. The pressure in the pipe in the loop was 4 kg/cm$^2$.

The AI concentration of the obtained neutralized product was 70% by weight and pH was 6.5. The neutralized product contained fatty acid methyl esters, α-sulfofatty acid methyl ester sodium salt, α-sulfofatty acid disodium salts (Di—Na), Glauber's salt, sodium methyl sulfate, sodium sulfite, sodium carboxylates, dimethyl ether and methanol.

The methanol concentration of the neutralized product was 2.2% based on the AI.

Bleaching Step for the Neutralized Product

Subsequently, the neutralized product was fed to a bleaching agent mixing line 14 at a feed rate of 164 kg/hr. The bleaching agent mixing line 14 was of a circulation loop type provided with a circulation line 16 having the heat exchanger 16a. 35% hydrogen peroxide water washed through the bleaching agent feed line 14' at a rate of 3.3 kg/hr (0.5% as pure compound based on the AI) to sufficiently mix it with the neutralized product already mixed with the bleaching agent (preliminarily bleached product) from the circulation line 16.

The circulation amount in the loop was 15 times that of the neutralized product to be freshly added to the preliminarily bleached product and the pressure inside the pipe in the circulation pipe was 4 kg/cm$^2$. The temperature of the circulation loop was controlled to 120° C. by the heat exchanger 16a and the residence time in the circulation loop was 10 minutes.

Then, the mixture was introduced into the bleaching line 15 of a flow pipe type to proceed the.bleaching. The bleaching line 15 was a double pipe with a jacket whose temperature and pressure could be adjusted.

The flow of the bleaching agent mixture was a piston flow adjusted to a pressure of 4 kg/cm$^2$ and a temperature of 120° C. and the residence time was 45 minutes.

The obtained bleached product contained fatty acid methyl esters, α-sulfofatty acid methyl ester sodium salt, α-sulfofatty acid disodium salts, Glauber's salt, sodium methyl sulfate, sodium sulfite, sodium carboxylates, dimethyl ether, methanol, hydrogen peroxide, oxygen, and carbon dioxide.

Deodorization Step: Flush Method

Subsequently, the bleached product was continuously introduced in the flush can 17 at a rate of 167 kg/hr and flushed at a normal pressure to deodorize it.

The evaporation amount removed from the discharge line 19 was 3.7 kg/hr. In the condensed water of the evaporated product, besides methanol, low boiling components which cause odor, for example, short chain fatty acid methyl esters, short chain carboxylic acids, ethers, ketones, and aldehydes were detected.

The obtained product contained fatty acid methyl esters, α-sulfofatty acid methyl ester sodium salt, α-sulfofatty acid disodium salts, Glauber's salt, sodium methyl sulfate, sodium sulfite, sodium carboxylates, dimethyl ether, methanol, and hydrogen peroxide.

The AI concentration of the product (the sum of α-sulfofatty acid alkyl ester salts and α-sulfofatty acid disodium salts) was 70.1% by weight and the viscosity was 60 poises at 50° C., which are physical properties which allow handling.

In Table 3, the reactivity, composition and color of the products is shown. The colors were values obtained by measuring 5% by weight ethanol solution or 5% by weight aqueous solution of sulfonic acid or AI on a Klett photoelectric photometer using a No. 42 Blue Filter having a light path length of 40 mm.

Notice that adherence to the apparatus indicates results obtained by stopping the apparatus at the point in time when the neutralized product had been produced for 3 hours and observing the state of adherence of α-sulfofatty acid disodium salts inside the apparatus.

Organoleptic evaluation of the odors before and after the deodorization step were performed by a panel of 5 panelists after completion of cooling the product to room temperature and the evaluation was based on the following criteria.

⊚: Substantially odorless;

○: Has a slight odor but masking with a perfume is possible;

Δ: Considerable odor is detected, masking with a perfume impossible;

X: Has a strong odor.

As a result, the evaluation of the product before the deodorization step was Δ and that of the product after the deodorization step was ⊚.

Further, the products were stored in a constant temperature room for 1 month and then evaluation was made in the same manner as described above. No change in the evaluation occurred.

Examples 2 to 4 and Comparative Examples 1 to 3

Under the conditions shown in Table 3, experiments were carried out in the same manner as in Example 1. The deodorization step was conducted only in Examples 3 and 4. The results are shown in Table 3 together.

Evaluation of odors in Examples 2 and 4 and Comparative Examples 1 to 3 in the same manner as in Example 1. Immediately after the production, the evaluation was Δ for each product and no change in evaluation occurred after 1 month. Further, the odors before and after the deodorization step in Examples 3 and 4 were evaluated in the same manner as in Example 1 and the same evaluation as in Example 1 was obtained in each product.

The results in Table 3 revealed that the color was improved by the coloring inhibitor and that even when the aqueous alkali solution and the AI concentration were both high, the neutralization step conducted in the presence of methanol inhibited the generation of α-sulfofatty acid disodium salts. Further, it revealed that no adherence to the apparatus occurred so that the production efficiency could be improved.

TABLE 3

|  | Example | | | | Comparative Example | | |
|---|---|---|---|---|---|---|---|
|  | 1 | 2 | 3 | 4 | 1 | 2 | 3 |
| Iodine value of raw material | 0.13 | | | | | | |
| Carbon chain length of raw material | C14/C16 = 2/8 | | | | | | |
| Coloring inhibitor* | (1) | (1) | (1) | (2) | — | — | (1) |
| (wt %) | 5% | 5% | 10% | 5% | | | |
| Esterification step | | | | | | | |
| Addition amount of methanol (wt % based on acid) | 4.0 | 8.0 | 4.0 | 2.0 | — | 2.0 | — |
| Neutralization step | | | | | | | |
| AI concentration (wt %) | 70.1 | 69.1 | 69.5 | 71.0 | 71.5 | 71.1 | 71.2 |
| Di-salt (wt % based on AI)** | 2.3 | 1.0 | 2.5 | 5.0 | 16.5 | 6.0 | 14.0 |
| Concentration of methanol (wt % based on AI) | 2.2 | 3.5 | 2.3 | 0.8 | 0 | 1.0 | 0 |
| Color (5% Klett) | 880 | 860 | 540 | 490 | 2100 | 1950 | 940 |
| Reactivity of raw material (%) | 99.0 | 99.2 | 99.2 | 99.2 | 97.5 | 97.8 | 99.0 |
| Adherence to apparatus | None | None | None | None | Exist | Exist | Exist |
| Bleaching step | | | | | | | |
| Addition amount of hydrogen peroxide (as pure compound) (wt %) | 0.5 | 0.5 | 0.5 | 0.5 | 0.5 | 0.5 | 0.5 |
| Color (5% Klett) | 33 | 34 | 26 | 25 | 155 | 150 | 120 |
| Di-salt (wt % based on AI) | 2.3 | 1.0 | 2.5 | 5.0 | 16.5 | 6.0 | 14.0 |
| Concentration of remaining methanol (wt % based on AI) | 1.2 | 2.4 | 1.2 | 0.2 | 0 | 0.4 | 0 |

*Coloring inhibitor: (1) $Na_2SO_4$, (2) $K_2SO_4$
**Di-salt: α-sulfofatty acid dialkali salts Examples 5 to 9 and Comparative Examples 4 to 6

Using raw materials having the carbon distributions shown in Table 5, introduction of the sulfonating gas and aging were carried out in the same manner as in Example 1. The concentration of $SO_3$ in the sulfonating gas was 7% by volume and the temperature upon aging was 85° C.

Subsequently, methanol in the amount shown in Table 4 was added and the mixture was stirred at 80° C. for 20 minutes to effect esterification. Then, a 35% by weight aqueous sodium hydroxide solution was used to neutralize the solution to pH 7 to 8 to obtain a neutralized product. Thereafter, the neutralized product was bleached under the conditions shown in Table 4. The results are shown in Table 4 together.

TABLE 4

|  | Example | | | | | Comparative Example | | |
|---|---|---|---|---|---|---|---|---|
|  | 5 | 6 | 7 | 8 | 9 | 4 | 5 | 6 |
| Iodine value of raw material (×10$^{-2}$) | 5 | 2 | 3 | 3 | 0.2 | 5 | 2 | 0.9 |
| Carbon chain length of raw material*** | (I) = 3/7 | (II) = 1/1 | (I) = 3/7 | (III) = 1/2/6/1 | (II) = 3/7 | (I) = 3/7 | (II) = 1/1 | (I) = 3/7 |
| Coloring inhibitor* | (1) | (1) | (2) | (1) | (1) | — | — | (1) |
| (wt %) | 5% | 5% | 1% | 5% | 3% | | | 5% |
| Esterification step | | | | | | | | |
| Addition amount of methanol (wt % based on acid) | 4.0 | 4.0 | 4.0 | 4.0 | 4.0 | 4.0 | 4.0 | — |
| Neutralization step | | | | | | | | |
| Concentration of aqueous alkali solution (wt %) | 35 | 35 | 35 | 35 | 35 | 35 | 35 | 35 |
| AI concentration (wt %) | 69.6 | 67.8 | 70.2 | 70.7 | 68.5 | 70.8 | 66.5 | 70.5 |
| Di-salt (wt % based on AI)** | 2.3 | 2.4 | 2.8 | 2.1 | 2.6 | 6.5 | 7.0 | 15.3 |
| Concentration of methanol (wt % based on AI) | 2.0 | 2.1 | 2.6 | 2.2 | 2.3 | 1.1 | 1.3 | 0 |
| Color (5% Klett) | 410 | 580 | 450 | 390 | 550 | 1200 | 1600 | 370 |

TABLE 4-continued

|  | Example | | | | | Comparative Example | | |
| --- | --- | --- | --- | --- | --- | --- | --- | --- |
|  | 5 | 6 | 7 | 8 | 9 | 4 | 5 | 6 |
| Reactivity of raw material (%) | 98.4 | 98.0 | 98.5 | 98.8 | 99.0 | 98.2 | 97.8 | 98.5 |
| Adherence to apparatus | None | None | None | None | None | Exist | Exist | Exist |
| Bleaching step | | | | | | | | |
| Addition amount of hydrogen peroxide (as pure compound) (wt %) | 1.0 | 0.5 | 0.5 | 0.5 | 1.0 | 1.0 | 0.5 | 0.2 |
| Reaction temperature (° C.) | 60 | 120 | 120 | 120 | 80 | 80 | 120 | 80 |
| Time (hr) | 6 | 1 | 1 | 0.5 | 6 | 6 | 1 | 6 |
| Color (5% Klett) | 75 | 28 | 25 | 32 | 80 | 280 | 300 | 95 |
| Di-salt (wt % based on AI) | 2.3 | 2.1 | 2.7 | 2.1 | 2.5 | 6.5 | 6.8 | 15.2 |
| Concentration of remaining methanol (wt % based on AI) | 1.5 | 1.3 | 1.8 | 1.4 | 1.7 | 0.5 | 0.4 | 0 |

*Coloring inhibitor: (1) $Na_2SO_4$, (2) $K_2SO_4$
Di-salt: α-sulfofatty acid dialkali salts
**Carbon chain length of raw material: (1) C14/C16, (II) C16/C18, (III) C12/C14/C16/C18

TABLE 5

|  | (I) | (II) | (III) |
| --- | --- | --- | --- |
| Composition (%) | | | |
| C10 | 0–1 | 0–1 | 0–1 |
| C12 | 0–1 | 0–1 | 5–20 |
| C14 | 18–35 | 1–3 | 10–50 |
| C16 | 65–82 | 20–60 | 40–70 |
| C17 | 0–2 | 0–2 | 0–2 |
| C18 | 0–1 | 40–80 | 5–30 |
| C20 | 0–1 | 0–2 | 0–2 |

From Table 4, it is revealed that in Examples 5 to 9 of the present invention, products having good color, a concentration of α-sulfofatty acid disodium salts which is low and a purity which is high were obtained.

Subsequently, the deodorization step (flush method) was performed in the same manner as in Example 1 and the odors were evaluated. Before the deodorization step, the evaluation was Δ for each product and after the deodorization step, the evaluation was ⊙. Further, the products were stored in a constant temperature room at 40° C. and after 1 month the evaluation was carried out in the same manner as described above. No change in evaluation occurred.

That is, the results shown in Tables 3 and 4 reveal that the overall interactions between the addition of coloring inhibitor, whether or not an esterification step is present, the addition amount of methanol (the remaining amount of methanol in the neutralization step), and the bleaching of the neutralized product enabled the elimination of the recovery of methanol and the improvement in color and purity of α-sulfofatty acid alkyl ester salts. By performing the deodorization step by a flush method, it was revealed that α-sulfofatty acid alkyl ester salts having less odor can be obtained by a simple operation.

Example 10

Sulfonation reaction was carried out using the pipe-type gas-liquid mixed phase flow reactor (pseudo-film reactor) as shown in FIG. 3 in place of the vessel-type reactor 1.

A 100-ml reaction mixer with a jacket as the introduction part 26 was used. As the reaction tube 32 with a jacket, four pieces of 2-m piping made of stainless SUS 316L having an inner diameter of 13.8 mm were used in parallel and these were connected to each other with connection pipes 34 of 13.8 mm in inner diameter and 2 m in length.

In the stirring vessel 21, raw material fatty acid methyl esters the same as those shown in Table 2 except that the iodine value was 0.05 and Glauber's salt (5% by weight based on the raw material) as the coloring inhibitor were charged and the mixture was heated at 50° C. to have Glauber's salt uniformly dispersed in the liquid phase and the pump 22 was activated to return the mixture to the stirring vessel 21 through the circulation pipe 24 to increase miscibility in order to prepare a solid-liquid mixed phase. At this time, the flow rates inside the extraction pipe 23, the circulation pipe 24 and the feed pipe 25 were each 0.7 m/sec and the inside pressure was each 2 kg/cm².

Subsequently, the solid-liquid mixed phase was fed to the introduction part 26 through the raw material introduction pipe 28 in a stable manner at a rate of 128 g/min. On the other hand, the sulfonating gas diluted with desiccated air to 8% by volume was introduced quantitatively at a rate of 0.3 m³/min through the sulfonating gas introduction pipe 29 in the same manner as in Example 1. At this time the temperature of the introduction part was 80° C. and the temperature of the solid-liquid mixed phase in the reaction tube 32 was adjusted to 80° C. by controlling cold water in the jacket.

The gas flowrate in the reaction tube 32 was 30 m/sec, the mean thickness of annular liquid film of raw material was 0.3 mm, the flowrate was 5 cm/sec and the residence time was 60 seconds.

The sulfonated product and exhaust gas were separated in the recovery part 36 and then the sulfonated product was introduced into the vessel-type reactor 1 shown in FIG. 2, followed by aging for 30 minutes while maintaining the reaction temperature at 80° C.

Thereafter, the steps of esterification to deodorization (flush method) were carried out in the same manner as in Example 1.

Table 6 shows the reactivity and the colors and compositions of the products.

Notice that the odors before and after the deodorization step were evaluated in the same manner as in Example 1. In each case, the same evaluations in Example 1 were obtained.

Example 11

In the same manner as in Example 10, sulfonation reaction was carried out using a pipe-type gas-liquid mixed phase flow reactor (pseudo-film reactor). However, as the introduction part 26, one having a volume of 500 ml with a jacket was used. As the reaction tube 32 on the upper part thereof, five tubes having an inner diameter of 13.8 mm and a length of 2 m were bundled and connected. The five reaction tubes 32 were arranged so that the reaction gas and solid-liquid mixed phase flowed in uniformly through the introduction part 26. The inner diameter of the connection pipe 34 and the reaction tube 32 downstream was each 31-mm.

The temperature of the introduction part 26 was adjusted to 80° C. and the temperature of the solid-liquid mixed phase in the reaction tube 32 was adjusted to 80° C. Thereafter, aging was carried out in the same manner as in Example 10 and the steps of esterification to deodorization were carried out in the same manner as in Example 1.

Table 6 shows the reactivity and the colors and compositions of the products.

Notice that the odors before and after the deodorization step were evaluated in the same manner as in Example 1. In each case, the same evaluations in Example 1 were obtained.

Example 12

The sulfonation step to the neutralization step were carried out in the same manner as in Example 1 to obtain a neutralized product. The neutralized product was once stored in a vat and then subjected to heat treatment.

That is, in a pilot apparatus of a loop+flow pipe type consisting of the bleaching agent mixing line 14 and the bleaching line 15 shown in FIG. 1, the neutralized product was fed at a rate of 55 kg/hr. At this time, no bleaching agent (hydrogen peroxide) was added through the bleaching agent feed line 14'. Inside the bleaching agent mixing line 14 and the bleaching line 15 were adjusted to a temperature of 120° C. and a pressure of 4 kg/cm², the residence time being 3 hours in total.

After the heat treatment, the flushed product flushed into the flush can 17 at a normal pressure had a color (5% Klett) of 320 and was improved as compared with the color immediately after the sulfonation (900).

Then, the same bleaching step as in Example 1 was carried out.

Table 6 shows the reactivity, the compositions and the colors of the products as measured by the same manner as in Example 1. It is revealed that the heat treatment improved the color.

Note that the odors before and after the deodorization step were evaluated in the same manner as in Example 1. In each case, the same evaluations in Example 1 were obtained.

Example 13

The sulfonation step to the neutralization step were carried out in the same manner as in Example 1 to obtain a sulfonated product. The esterified sulfonated product and sodium carbonate were quantitatively to Kurimoto KRC Kneader to mix and neutralize the product. At this time, the residence time was about 10 minutes and the neutralization temperature was 60 to 70° C.

After the neutralization, bleaching was performed in a similar manner to that in Example 1 using 1% hydrogen peroxide as pure compound under the conditions of a pressure inside the pipe of 4 kg/cm², a temperature of 120° C., and a residence time of 1 hour and then the deodorization step was carried out by an adsorption method using activated carbon.

More particularly, a slurry of the neutralized product after bleaching was kept in a vessel at 90° C. while stirring and mixing, and the low boiling components (odor components) were expelled to the gas phase. Then, the gas phase containing the odor components was led to an activated carbon fixed layer to have the odor components adsorbed by the activated carbon. The temperature of the inlet to the activated carbon fixed layer was cooled to 30° C. before the operation was performed. Note that as the activated carbon, coconut shell based powdery activated carbon was used.

Table 6 shows the reactivity, the compositions and the colors of the products as measured in the same manner as in Example 1.

Notice that the odors before and after the deodorization step were evaluated in the same manner as in Example 1. In each case, the same evaluations as in Example 1 were obtained.

TABLE 6

| Item | Example 10 | Example 11 | Example 12 | Example 13 |
|---|---|---|---|---|
| AI (%) | 69.2 | 69.5 | 69.0 | 83.1 |
| Methyl sulfate (% based on AI) | 7.5 | 7.3 | 7.4 | 7.2 |
| Glauber's salt (% based on AI) | 2.4 | 2.5 | 2.4 | 2.4 |
| Di-Na (% based on AI)* | 2.6 | 2.4 | 2.3 | 2.5 |
| Remaining methanol (% based on AI) | 1.2 | 1.3 | 1.0 | 1.0 |
| Remaining hydrogen peroxide (% based on AI) | 0.05 | 0.05 | 0.06 | 0.05 |
| Reactivity (%) | 98.5 | 98.5 | 99.0 | 98.7 |
| Color (5% Klett) | 37 | 38 | 20 | 43 |

*Di-Na: α-sulfofatty acid di-Na salts

INDUSTRIAL APPLICABILITY

As explained above, in the production method of the present invention no esterification is performed simultaneously with bleaching unlike in conventional methods, so that in the esterification step, the consumption of lower alcohols due to side reactions due to the action of the bleaching agent is lower in amount. Also, in the neutralization step, side reactions are inhibited so that the amount of lower alcohol consumed can be reduced.

As a result, the addition amount of lower alcohol may be adjusted such that the amount necessary for the inhibition of a decrease in viscosity and production of by-products in the neutralization step in addition to the amount necessary for esterification will remain so that it can be set to an addition amount less than is used conventionally. Therefore, the amount of the lower alcohol remaining in the commercial product is small and hence there is no need for recovery, purification and recycling of lower alcohols, enabling simplification of the production step.

Further, sulfonation in the presence of a coloring inhibitor can give rise to α-sulfofatty acid alkyl ester salts having pale colors close to white.

Also, preferably by performing the deodorization step, the odor of α-sulfofatty acid alkyl ester salts themselves can be improved so that the formulation of the detergent composition is not limited unlike the conventional method and no complicated treatment of fatty acid alkyl esters is necessary.

In the deodorization step, in particular use of a flush method enables effective removal of odors by a simple operation.

What is claimed is:

1. A method for α-sulfofatty acid alkyl ester salts comprising a sulfonation step for bring a fatty acid alkyl ester into contact with a sulfonating gas in the presence of a coloring inhibitor to sulfonate the fatty acid alkyl ester; an esterification step for esterifying the product of the sulfonation step with a lower alcohol; a neutralization step for neutralizing the esterified product of the esterification step to obtain a neutralized product; and a bleaching step for bleaching the neutralized product to obtain a bleached product.

2. The method for α-sulfofatty acid alkyl ester salts as claimed in claim 1, further comprising a deodorization step for deodorizing the bleached product.

3. The method for α-sulfofatty acid alkyl ester salts as claimed in claim 2, wherein the deodorization in the deodorization step is performed by a flush method.

* * * * *